US009797911B2

(12) United States Patent
Keshet et al.

(10) Patent No.: US 9,797,911 B2
(45) Date of Patent: Oct. 24, 2017

(54) COMPOSITION FOR USE IN DETECTION OF SFLT-14

(71) Applicants: Yissum Research Development Company of the Hebrew University of Jerusalem Ltd., Jerusalem (IL); Hadasit Medical Research Services and Development Ltd., Jerusalem (IL)

(72) Inventors: Eli Keshet, Moshav Aminadav (IL); Shay Sela, Haifa (IL); Ahuva Itin, Jerusalem (IL); Simcha Yagel, Jerusalem (IL)

(73) Assignees: Yissum Research Development Company of the Hebrew University of Jerusalem Ltd., Jerusalem (IL); Hadasit Medical Research Services and Development Ltd., Jerusalem (IL)

( * ) Notice: Subject to any disclaimer, the term of this patent is extended or adjusted under 35 U.S.C. 154(b) by 475 days.

(21) Appl. No.: 14/304,948

(22) Filed: Jun. 15, 2014

(65) Prior Publication Data

US 2014/0295454 A1 Oct. 2, 2014

Related U.S. Application Data

(62) Division of application No. 13/685,892, filed on Nov. 27, 2012, which is a division of application No. 12/448,404, filed as application No. PCT/IL2007/001589 on Dec. 20, 2007, now abandoned.

(60) Provisional application No. 60/875,822, filed on Dec. 20, 2006.

(51) Int. Cl.
*C07K 16/00* (2006.01)
*G01N 33/68* (2006.01)
*C07K 14/71* (2006.01)

(52) U.S. Cl.
CPC ........... *G01N 33/689* (2013.01); *C07K 14/71* (2013.01)

(58) Field of Classification Search
None
See application file for complete search history.

(56) References Cited

U.S. PATENT DOCUMENTS

| 6,710,174 | B2 | 3/2004 | Bennett et al. |
| 7,939,634 | B2 | 5/2011 | Ayalon-Soffer et al. |
| 2004/0126828 | A1 | 7/2004 | Karumanchi et al. |
| 2010/0075891 | A1 | 3/2010 | Ayalon-Soffer et al. |
| 2010/0136012 | A1 | 6/2010 | Keshet et al. |
| 2013/0084583 | A1 | 4/2013 | Keshet et al. |

FOREIGN PATENT DOCUMENTS

| WO | WO 01/64835 | 9/2001 |
| WO | WO 2005/072340 | 8/2005 |
| WO | WO 2006/033664 | 3/2006 |
| WO | WO 2006/069373 | 6/2006 |
| WO | WO 2007/039903 | 4/2007 |
| WO | WO 2008/075363 | 7/2008 |

OTHER PUBLICATIONS

Advisory Action Before the Filing of an Appeal Brief Dated Feb. 20, 2014 U.S. Appl. No. 13/685,892.
Communication Pursuant to Article 94(3) EPC Dated Dec. 11, 2009 From the European Patent Office Re.: Application No. 07849615.5.
International Preliminary Report on Patentability Dated Jul. 2, 2009 From the International Bureau of WIPO Re.: Application No. PCT/IL2007/001589.
International Search Report and the Written Opinion Dated Apr. 28, 2008 From the International Searching Authority Re.: Application No. PCT/IL2007/001589.
Invitation Pursuant to Article 94(3) and Rule 71(1) EPC Dated Oct. 22, 2010 From the European Patent Office Re. Application No. 07849615.5.
Office Action Dated Jul. 3, 2012 From the Israel Patent Office Re. Application No. 199407 and Its Translation Into English.
Office Action Dated Mar. 4, 2013 From the Israel Patent Office Re. Application No. 199407 and Its Translation Into English.
Official Action Dated Feb. 3, 2012 U.S. Appl. No. 12/448,404.
Official Action Dated Feb. 4, 2013 U.S. Appl. No. 13/685,892.
Official Action Dated Aug. 13, 2013 U.S. Appl. No. 13/685,892.
Official Action Dated Jun. 27, 2012 U.S. Appl. No. 12/448,404.
Restriction Official Action Dated Nov. 15, 2011 U.S. Appl. No. 12/448,404.
Translation of Notice of Reason for Rejection Dated Nov. 27, 2012 From the Japanese Patent Office Re. Application No. 2009-542395.
Ayalon-Soffer et al. "Human HSFLT_PEA_1_P10 Protein Fragment", Database Geneseq [Online], XP002476507, Retrieved From EBI Accession No. GSP: AEK17175, Database Accession No. AEK17175, Nov. 2, 2006. Abstract.
Coleman "Of Mouse and Man—What Is the Value of the Mouse in Predicting Gene Expression in Huamns?", Drug Discovery Today. DDT, 8(6): 233-235, Mar. 2003.
Geisler et al. "Differential Distribution of Five Members of the Matrix Metalloproteinase Family and One Inhibitor (TIMP-1) in Human Liver and Skin", Cell Tissue Research, 289: 173-183, 1997.
Liu et al. "Comparison of Differentially Expressed Genes in T Lymphocytes Between Human Autoimmune Disease and Murine Models of Autoimmune Disease", Clinical Immunology, 112: 225-230, 2004.
Min et al. "Variability of Gene Expression Profiles in Human Blood and Lymphoblastoid Cell Lines", BioMed Central, BMC Genomics, 11(96): 1-14, 2010.
Saetre et al. "From Wild Wolf to Domestic Dog: Gene Expression Changes in the Brain", Molecular Brain Research, 126: 198-206, 2004.

*Primary Examiner* — Christine J Saoud

(57) ABSTRACT

An isolated polypeptide comprising an amino acid sequence at least 70% homologous to SEQ ID NO: 4 and an isolated polynucleotide encoding same are disclosed. A polynucleotide comprising a nucleic acid sequence capable of specifically hybridizing to the isolated polynucleotide and an isolated antibody comprising an antigen recognition domain which specifically binds the isolated polypeptide are also disclosed. Pharmaceutical compositions, methods of diagnosing and treating comprising same are also disclosed.

6 Claims, 11 Drawing Sheets
(7 of 11 Drawing Sheet(s) Filed in Color)

(56) References Cited

OTHER PUBLICATIONS

Sela et al. "A Novel Human-Specific Soluble Vascular Endothelial Growth Factor Receptor 1: Cell Type-Specific Splicing and Implications to Vascular Endothelial Growth Factor Homeostasis and Preeclampsia", Circulation Research, 102: 1566-1574, 2008.

Sella-Tavor et al. "Human VEGFR1 Precursor Protein HSFLT_P10", Database Geneseq [Online], Retrieved From EBI Accession No. GSP:AFR05586, Databse Accession No. AFR05586, Jul. 26, 2007. Abstract.

Shibuya et al. "Signal Transduction by VEGF Receptors in Regulation of Angiogenesis and Lymphangiogenesis", Experimental Cell Research, 312(5): 549-560, Mar. 2006. p. 549-560.

Tang et al. "Human Polypeptide SEQ ID No. 18685", Database Geneseq [Online], XP002476508, Retrieved From EBI Accession No. GSP:AA004793, Database Accession No. AA004793, Nov. 6, 2001. Abstract.

Thomas et al. "Intronic Polyadenylation Signal Sequences and Alternate Splicing Generate Human Soluble Flt1 Variants and Regulate the Abundance of Soluble Flt1 in the Placenta", The FASEB Journal, 21: 3885-3895, 2007.

Vuorela et al. "Amniotic Fluid-Soluble Vascular Endothelial Growth Factor Receptor-1 in Preeclampsia", Obstetrics and Gynecology, 95(3): 353-357, Mar. 2000. p. 353-357.

CCTCCTGCGAAACCTCAGTGATCAGTGGCCATCAGCAGTTCCACCACTTAGATGTCATGGTGTC
CCGAGGTCAGATCATTGGTTAAACAACATACACAGAGACGTGAACTGTATACACAAGGTAC
CATGGTCCGTCATCATCATCAGTGTCATCATCGTCATCATCATCATCGTCATCATCTAGCTATCATCATTAT
CATCATCATCATCATCATAGCTATCATCATTATTGAAAACTATTGTGTCAACTTCAAAGAACTATCCTTA
GTTGGAGAGCCAAGACAATCATAACAATAACAAATGGCCGGGCATGGTGGCTCACGCCCTGTAATCCCAGCACTT
GGGAGGCCAAGCAGGCAGGATCATTTGAGGTCAGGAGTCAAGACCAGCCTGACCAAGATGGTGAAATGTC
TCTATTAAAATACAAAATTAGCCAGGTGGTGGCTGTAATGCCAGCTACTGGGAGGCTGAGACAG
GAGAATCACTTGAACCCAGGAGGCAGAGGTTGCAGTGAGCCGAGATCGTGTACTGCACTCCAGCCTGGGCAACA
AGAGCGAAACTCCGTCTCAAAAAACAAAATAAATAAACAGACAAAATTCACTTTTATCTATTAAA
CTTAACATACATGCTAAAAAAAAAAAAAAAA   (SEQ. ID. NO: 7)

Fig. 2A

MetVSYWDTGVLLCALLSCLLLTGSSGSKLKDPELSLKGTQHIMQ
AGQTLHLQCRGEAAHKWSLPEMVSKESERLSITKSACGRNGKQF
CSTLTNTAQANHTGFYSCKYLAVPTSKKKETESAIYIFISDTGRP
FVEMYSEIPEIIHMTEGRELVIPCRVTSPNITVTLKKFPLDTLIPDG
KRIIWDSRKGFIISNATYKEIGLLTCEATVNGHLYKTNYLTHRQTN
TIIDVQISTPRPVKLLRGHTLVLNCTATTPLNTRVQMTWSYPDEKN
KRASVRRRIDQSNHANIFYSVLTIDKMQNKDKGLYTCRVRSGPS
FKSVNTSVHIYDKAFITVKHRKQQVLETVAGKRSYRLSMKVKAFP
SPEVVWLKDGLPATEKSARYLTRGYSLIIKDVTEEDAGNYTILLSI
KQSNVFKNLTATLIVNVKPQIYEKAVSSFPDPALYPLGSRQILTCT
AYGIPQPTIKWFWHPCNHNHSEARCDFCSNNEESFILDADSNMG
NRIESITQRMAIIEGKNKMASTLVVADSRISGIYICIASNKVGTVGR
NISFYITDVPNGFHVNLEKMPTEGEDLKLSCTVNKFLYRDVTWILL
RTVNNRTIMHYSISKQKMAITKEHSITLNLTIMNVSLQDSGTYACRA
RNVYTGEEILQKEITRDQEAPYLLRNLSDHTVAISSSTTLDCHA
NGVPEPQITWFKNNHKIQQEPELYTSTSPSSSSPLSSSSSS
SSSStop
(SEQ. ID. NO: 2)

Ex14 ←
← Int14

Fig. 3A

Anti Exon 14 — <u>CHANGVPEPQITWFK</u> (CHFK, SEQ. ID. NO: 6)

Anti Intron 14 — <u>CELYTSTSPSSSSSS</u> (CESS, SEQ. ID. NO: 5)

Fig. 3B

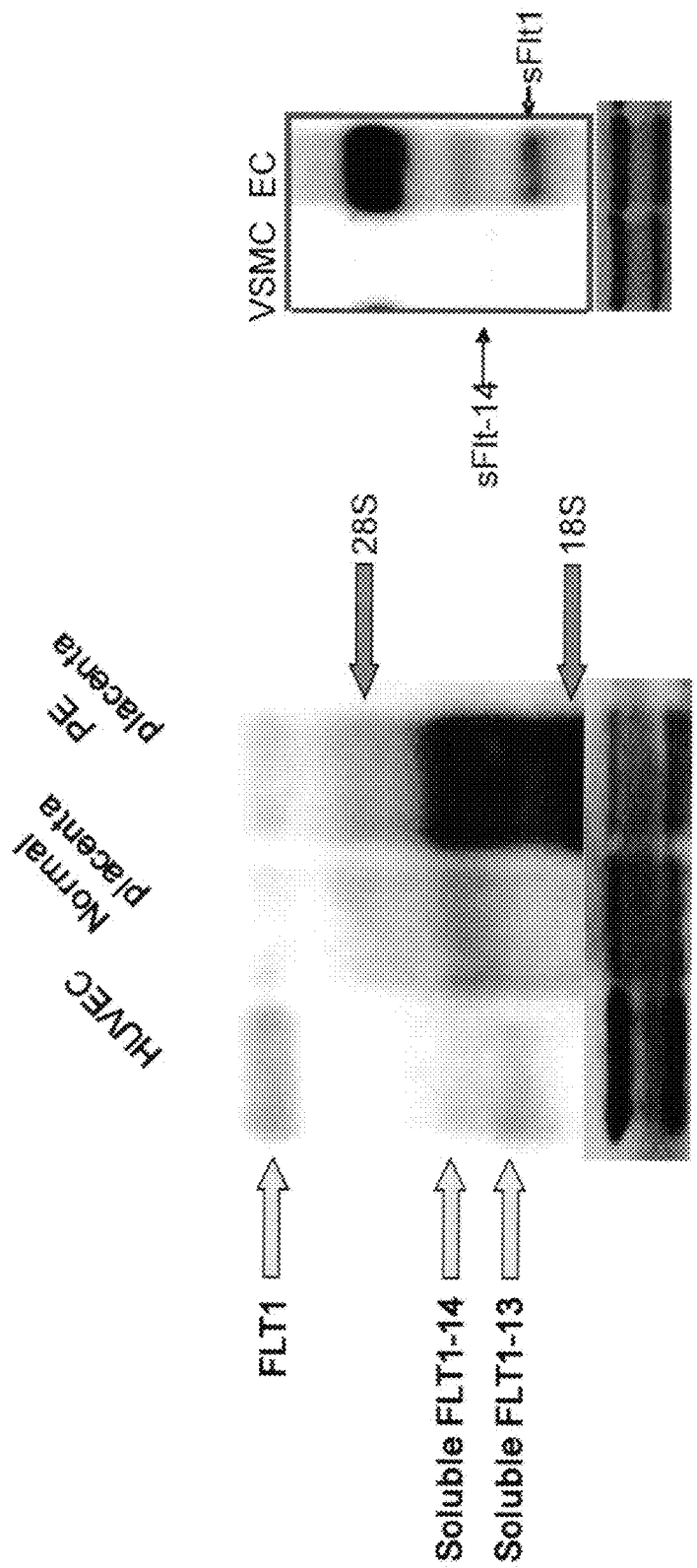

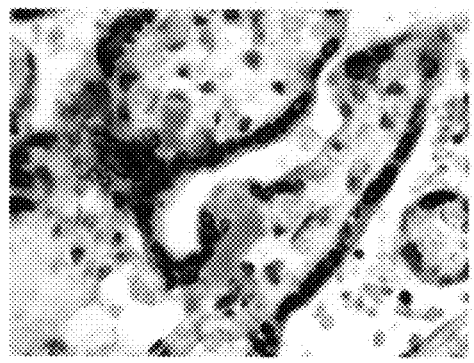 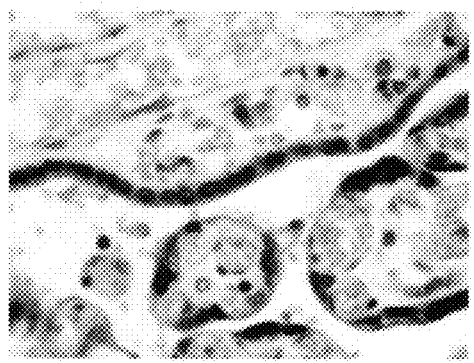
Fig. 5A  Fig. 5B
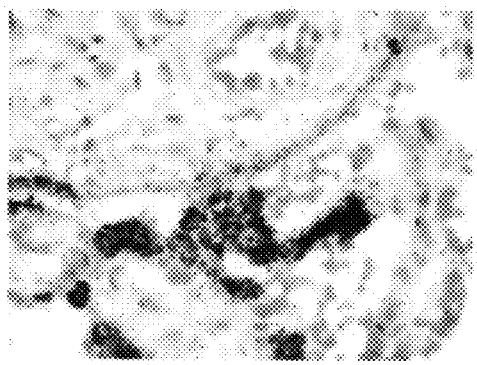 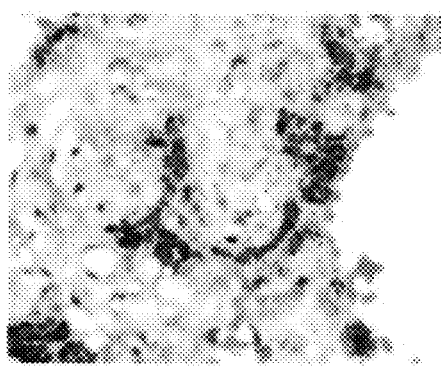
Fig. 5C  Fig. 5D
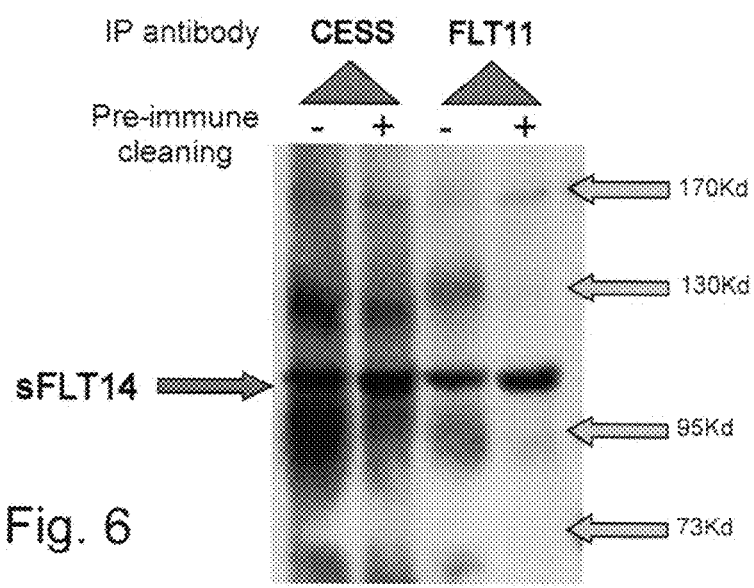
Fig. 6

Protein = vascular endothelial growth factor receptor [Homo sapiens] [56285330]
1 MVSYWDTGVL LCALLSCLLL TGSSSGSKLK DPELSLKGTQ HIMQAGQTLH
51 LQCRGEAAHK WSLPEMVSKE SERLSITKSA CGRNGKQFCS TLTLNTAQAN
101 HTGFYSCKYL AVPTSKKKET ESAIYIFISD TGRPFVEMYS EIPEIIHMTE
151 GRELVIPCRV TSPNITVTLK KFPLDTLIPD GKRIIWDSRK GFIISNATYK
201 EIGLLTCEAT VNGHLYKTNY LTHRQTNTII DVQISTPRPV KLLRGHTLVL
251 NCTATTPLNT RVQMTWSYPD EKNKRASVRR RIDQSNSHAN IFYSVLTIDK
301 MQNKDKGLYT CRVRSGPSFK SVNTSVHIYD KAFITVKHRK QQVLETVAGK
351 RSYRLSMKVK APPSPEVVWL KDGLPATEKS ARYLTRGYSL IIKDVTEEDA
401 GNYTILLSIK QSNVFKNLTA TLIVNVKPQI YEKAVSSFPD PALYPLGSRQ
451 ILTCTAVGIP QPTIKWFWHP CNHNHSEARC DFCSNNEESS ILDADSNMGN
501 RIESITQRMA IIEGKNKMAS TLVVADSRIS GIYICIASNK VGTVGRNISF
551 YITDVPNGFH VNLEKMPTEG EDLKLSCTVN KFLYRDVTWI LLRTVNNRTM
601 HYSISKQKMA ITKEHSITLN LTIMNVSLQD SGTYACRARN VYTGEEILQK
651 KEITIRDQEA PYLLRNLSDH TVAISSSTTL DCHANGVPEP QITWFKNHHK
701 IQQEPGIILG PGSSTLFIER VTEEDEGVYH CKATNQKGSV ESSAYLTVQG
751 TSDKSNLELI TLTCTCVAAT LFWLLLTLFI RKMKRSSSEI KTDYLSIIMD
801 PDEVPLDEQC ERLPYDASKW EFARERLKLG KSLGRGAFGK VVQASAFGIK
851 KSPTCRTVAV KMLKEGATAS EYKALMTELK ILTHIGHHLN VVNLLGACTK
901 QGGPLMVIVE YCKYGNLSNY LKSKRDLFFL NKDAALHMEP KKEKMEPGLE
951 QGKKPRLDSV TSSESFASSG FQEDKSLSDV EEEEDSDGFY KEPITMEDLI
1001 SYSFQVARGM EFLSSRKCIH RDLAARNILL SENNVVKICD FGLARDIYKN
1051 PDYVRKGDTR LPLKWMAPES IFDKIYSTKS DVWSYGVLLW EIFSLGGSPY
1101 PGVQMDEDFC SRLREGMRMR APEYSTPEIY QIMLDCWHRD PKERPRFAEL
1151 VEKLGDLLQA NVQQDGKDYI PINAILTGNS GFTYSTPAFS EDFFKESISA
1201 PKFNSGSSDD VRYVNAFKFM SLERIKTFEE LLPNATSMFD DYQGDSSTLL
1251 ASPMLKRFTW TDSKPKASLK IDLRVTSKSK ESGLSDVSRP SFCHSSCGHV
1301 SEGKRRFTYD HAELERKIAC CSPPPDYNSV VLYSTPPI Coverage: 3% Peptides:
434 AVSSFFPDPALYPLGSR → SEQ ID NO: 17
640 NVYTGEEILQK → SEQ ID NO: 18
657 DQEAPYLLR → SEQ ID NO: 19

SEQ ID NO: 16

Fig. 7

CESS antibody

Control

SEQUENCE LISTING

<160> NUMBER OF SEQ ID NOS: 19

<210> SEQ ID NO 1
<211> LENGTH: 2202
<212> TYPE: DNA
<213> ORGANISM: Homo sapiens

<400> SEQUENCE: 1

| | | | | | | |
|---|---|---|---|---|---|---|
| atggtcagct | actgggacac | cggggtcctg | ctgtgcgcgc | tgctcagctg | tctgcttctc | 60 |
| acaggatcta | gttcaggttc | aaaattaaaa | gatcctgaac | tgagtttaaa | aggcacccag | 120 |
| cacatcatgc | aagcaggcca | gacactgcat | ctccaatgca | ggggggaagc | agcccataaa | 180 |
| tggtctttgc | ctgaaatggt | gagtaaggaa | agcgaaaggc | tgagcataac | taaatctgcc | 240 |
| tgtggaagaa | atggcaaaca | attctgcagt | actttaacct | tgaacacagc | tcaagcaaac | 300 |
| cacactggct | tctacagctg | caaatatcta | gctgtaccta | cttcaaagaa | gaaggaaaca | 360 |
| gaatctgcaa | tctatatatt | tattagtgat | acaggtagac | ctttcgtaga | gatgtacagt | 420 |
| gaaatccccg | aaattataca | catgactgaa | ggaagggagc | tcgtcattcc | ctgccgggtt | 480 |
| acgtcaccta | acatcactgt | tactttaaaa | aagtttccac | ttgacacttt | gatccctgat | 540 |
| ggaaaacgca | taatctggga | cagtagaaag | ggcttcatca | tatcaaatgc | aacgtacaaa | 600 |
| gaaatagggc | ttctgacctg | tgaagcaaca | gtcaatgggc | atttgtataa | gacaaactat | 660 |
| ctcacacatc | gacaaaccaa | tacaatcata | gatgtccaaa | taagcacacc | acgcccagtc | 720 |
| aaattactta | gaggccatac | tcttgtcctc | aattgtactg | ctaccactcc | cttgaacacg | 780 |
| agagttcaaa | tgacctggag | ttaccctgat | gaaaaaaata | gagagcttc | cgtaaggcga | 840 |
| cgaattgacc | aaagcaattc | ccatgccaac | atattctaca | gtgttcttac | tattgacaaa | 900 |
| atgcagaaca | agacaaagg | actttatact | tgtcgtgtaa | ggagtggacc | atcattcaaa | 960 |
| tctgttaaca | cctcagtgca | tatatatgat | aaagcattca | tcactgtgaa | acatcgaaaa | 1020 |
| cagcaggtgc | ttgaaaccgt | agctggcaag | cggtcttacc | ggctctctat | gaaagtgaag | 1080 |
| gcatttcct | cgccggaagt | tgtatggtta | aagatgggt | tacctgcgac | tgagaaatct | 1140 |
| gctcgctatt | tgactcgtgg | ctactcgtta | attatcaagg | acgtaactga | agaggatgca | 1200 |
| gggaattata | caatcttgct | gagcataaaa | cagtcaaatg | tgtttaaaaa | cctcactgcc | 1260 |
| actctaattg | tcaatgtgaa | accccagatt | tacgaaaagg | ccgtgtcatc | gtttccagac | 1320 |
| ccggctctct | acccactggg | cagcagacaa | atcctgactt | gtaccgcata | tggtatccct | 1380 |
| caacctacaa | tcaagtggtt | ctggcacccc | tgtaaccata | atcattccga | agcaaggtgt | 1440 |
| gactttgtt | ccaataatga | agagtccttt | atcctggatg | ctgacagcaa | catgggaaac | 1500 |
| agaattgaga | gcatcactca | gcgcatggca | ataatagaag | gaaagaataa | gatggctagc | 1560 |
| accttggttg | tggctgactc | tagaatttct | ggaatctaca | tttgcatagc | ttccaataaa | 1620 |
| gttgggactg | tgggaagaaa | cataagcttt | tatatcacag | atgtgccaaa | tgggtttcat | 1680 |
| gttaacttgg | aaaaaatgcc | gacggaagga | gaggacctga | aactgtcttg | cacagttaac | 1740 |
| aagttcttat | acagagacgt | tacttggatt | ttactgcgga | cagttaataa | cagaacaatg | 1800 |
| cactacagta | ttagcaagca | aaaaatggcc | atcactaagg | agcactccat | cactcttaat | 1860 |
| cttaccatca | tgaatgtttc | cctgcaagat | tcaggcacct | atgcctgcag | agccaggaat | 1920 |
| gtatacacag | gggaagaaat | cctccagaag | aaagaaatta | caatcagaga | tcaggaagca | 1980 |
| ccatacctcc | tgcgaaacct | cagtgatcac | acagtggcca | tcagcagttc | caccacttta | 2040 |
| gactgtcatg | ctaatggtgt | ccccgagcct | cagatcactt | ggtttaaaaa | caaccacaaa | 2100 |

```
atacaacaag agcctgaact gtatacatca acgtcaccat cgtcatcgtc atcatcacca    2160
ttgtcatcat catcatcatc gtcatcatca tcatcatcat ag                      2202
```

<210> SEQ ID NO 2
<211> LENGTH: 733
<212> TYPE: PRT
<213> ORGANISM: Homo sapiens

<400> SEQUENCE: 2

```
Met Val Ser Tyr Trp Asp Thr Gly Val Leu Leu Cys Ala Leu Leu Ser
1               5                   10                  15

Cys Leu Leu Thr Gly Ser Ser Gly Ser Lys Leu Lys Asp Pro
            20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65              70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350
```

-continued

```
Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Glu Leu Tyr Thr Ser Thr Ser Pro Ser Ser Ser Ser Ser Ser Pro
705                 710                 715                 720

Leu Ser Ser Ser Ser Ser Ser Ser Ser Ser Ser
                725                 730
```

<210> SEQ ID NO 3
<211> LENGTH: 233
<212> TYPE: DNA
<213> ORGANISM: Homo sapiens
<220> FEATURE:
<221> NAME/KEY: misc_feature
<223> OTHER INFORMATION: Nucleic acid sequence encoding a unique 28 a.a.
      polypeptide portion of sFlt-14

<400> SEQUENCE: 3

```
atcaggaagc accatacctc ctgcgaaacc tcagtgatca cacagtggcc atcagcagtt    60
ccaccacttt agactgtcat gctaatggtg tccccgagcc tcagatcact tggtttaaaa   120
acaaccacaa aatacaacaa gagcctgaac tgtatacatc aacgtcacca tcgtcatcgt   180
catcatcacc attgtcatca tcatcatcat cgtcatcatc atcatcatca tag          233
```

<210> SEQ ID NO 4
<211> LENGTH: 28
<212> TYPE: PRT
<213> ORGANISM: Homo sapiens
<220> FEATURE:
<221> NAME/KEY: misc_feature
<223> OTHER INFORMATION: A unique 28 a.a. polypeptide portion of sFlt-14

<400> SEQUENCE: 4

```
Glu Leu Tyr Thr Ser Thr Ser Pro Ser Ser Ser Ser Ser Pro Leu
1               5                   10                  15

Ser Ser Ser Ser Ser Ser Ser Ser Ser Ser Ser Ser
            20                  25
```

<210> SEQ ID NO 5
<211> LENGTH: 15
<212> TYPE: PRT
<213> ORGANISM: Artificial sequence
<220> FEATURE:
<223> OTHER INFORMATION: A synthetic peptide used to generate a specific
      sFlt-14 antibody (CESS)

<400> SEQUENCE: 5

```
Cys Glu Leu Tyr Thr Ser Thr Ser Pro Ser Ser Ser Ser Ser Ser
1               5                   10                  15
```

<210> SEQ ID NO 6
<211> LENGTH: 15
<212> TYPE: PRT
<213> ORGANISM: Artificial sequence
<220> FEATURE:
<223> OTHER INFORMATION: A synthetic peptide used to generate a
      non-specific sFlt-14 antibody (CHFK)

<400> SEQUENCE: 6

```
Cys His Ala Asn Gly Val Pro Glu Pro Gln Ile Thr Trp Phe Lys
1               5                   10                  15
```

<210> SEQ ID NO 7
<211> LENGTH: 712
<212> TYPE: DNA
<213> ORGANISM: Homo sapiens
<220> FEATURE:
<221> NAME/KEY: misc_feature
<223> OTHER INFORMATION: A portion of sFlt-14 starting from exon 14 to
      the poly A tail

<400> SEQUENCE: 7

```
cctcctgcga aacctcagtg atcacacagt ggccatcagc agttccacca ctttagactg    60
tcatgctaat ggtgtccccg agcctcagat cacttggttt aaaaacaacc acaaaataca   120
acaagagcct gaactgtata catcaacgtc accatcgtca tcgtcatcat caccattgtc   180
atcatcatca tcatcgtcat catcatcatc atcatagcta tcatcattat catcatcatc   240
atcatcatca tcatagctac catttattga aaactattat gtgtcaactt caaagaactt   300
```

```
atcctttagt tggagagcca agacaatcat aacaataaca aatggccggg catggtggct    360
cacgcctgta atcccagcac tttgggaggc caaggcaggt ggatcatttg aggtcaggag    420
tccaagacca gcctgaccaa gatggtgaaa tgctgtctct attaaaaata caaaattagc    480
caggcatggt ggctcatgcc tgtaatgcca gctactcggg aggctgagac aggagaatca    540
cttgaaccca ggaggcagag gttgcaggga ccgagatcg tgtactgcac tccagcctgg    600
gcaacaagag cgaaactccg tctcaaaaaa caaataaata aataaataaa taaacagaca    660
aaattcactt tttattctat taaacttaac atacatgcta aaaaaaaaa aa            712
```

<210> SEQ ID NO 8
<211> LENGTH: 30
<212> TYPE: DNA
<213> ORGANISM: Homo sapiens
<220> FEATURE:
<221> NAME/KEY: misc_feature
<223> OTHER INFORMATION: sFlt-14 specific bridging region
<400> SEQUENCE: 8

```
aaattacaat cagagatcag gaagcaccat                                      30
```

<210> SEQ ID NO 9
<211> LENGTH: 2065
<212> TYPE: DNA
<213> ORGANISM: Homo sapiens
<400> SEQUENCE: 9

```
atggtcagct actgggacac cggggtcctg ctgtgcgcgc tgctcagctg tctgcttctc     60
acaggatcta gttcaggttc aaaattaaaa gatcctgaac tgagtttaaa aggcacccag    120
cacatcatgc aagcaggcca gacactgcat ctccaatgca ggggggaagc agcccataaa    180
tggtctttgc ctgaaatggt gagtaaggaa agcgaaaggc tgagcataac taaatctgcc    240
tgtggaagaa atggcaaaca attctgcagt actttaacct tgaacacagc tcaagcaaac    300
cacactggct tctacagctg caaatatcta gctgtaccta cttcaaagaa gaaggaaaca    360
gaatctgcaa tctatatatt tattagtgat acaggtagac ctttcgtaga gatgtacagt    420
gaaatccccg aaattataca catgactgaa ggaagggagc tcgtcattcc ctgccgggtt    480
acgtcaccta acatcactgt tactttaaaa aagtttccac ttgacacttt gatccctgat    540
ggaaaacgca taatctggga cagtagaaag ggcttcatca tatcaaatgc aacgtacaaa    600
gaaatagggc ttctgacctg tgaagcaaca gtcaatgggc atttgtataa gacaaactat    660
ctcacacatc gacaaaccaa tacaatcata gatgtccaaa taagcacacc acgcccagtc    720
aaattactta gaggccatac tcttgtcctc aattgtactg ctaccactcc cttgaacacg    780
agagttcaaa tgacctggag ttaccctgat gaaaaaaata gagagcttc cgtaaggcga    840 cgaattgacc aaagcaattc ccatgccaac atattctaca gtgttcttac tattgacaaa    900
atgcagaaca agacaaagg actttatact tgtcgtgtaa ggagtggacc atcattcaaa    960
tctgttaaca cctcagtgca tatatatgat aaagcattca tcactgtgaa acatcgaaaa    1020
cagcaggtgc ttgaaaccgt agctggcaag cggtcttacc ggctctctat gaaagtgaag    1080
gcatttccct cgccggaagt tgtatggtta aaagatgggt tacctgcgac tgagaaatct    1140
gctcgctatt tgactcgtgg ctactcgtta attatcaagg acgtaactga agaggatgca    1200
gggaattata caatcttgct gagcataaaa cagtcaaatg tgtttaaaaa cctcactgcc    1260
actctaattg tcaatgtgaa accccagatt tacgaaaagg ccgtgtcatc gtttccagac    1320
```

```
ccggctctct acccactggg cagcagacaa atcctgactt gtaccgcata tggtatccct    1380
caacctacaa tcaagtggtt ctggcacccc tgtaaccata atcattccga agcaaggtgt    1440
gacttttgtt ccaataatga agagtccttt atcctggatg ctgacagcaa catgggaaac    1500
agaattgaga gcatcactca gcgcatggca ataatagaag gaaagaataa gatggctagc    1560
accttggttg tggctgactc tagaatttct ggaatctaca tttgcatagc ttccaataaa    1620
gttgggactg tgggaagaaa cataagcttt tatatcacag atgtgccaaa tgggtttcat    1680
gttaacttgg aaaaaatgcc gacggaagga gaggacctga actgtcttg cacagttaac     1740 aagttcttat acagagacgt tacttggatt ttactgcgga cagttaataa cagaacaatg    1800
cactacagta ttagcaagca aaaaatggcc atcactaagg agcactccat cactcttaat    1860
cttaccatca tgaatgtttc cctgcaagat tcaggcacct atgcctgcag agccaggaat    1920
gtatacacag gggaagaaat cctccagaag aaagaaatta caatcagagg tgagcactgc    1980
aacaaaaagg ctgttttctc tcggatctcc aaatttaaaa gcacaaggaa tgattgtacc    2040
acacaaagta atgtaaaaca ttaaa                                          2065

<210> SEQ ID NO 10
<211> LENGTH: 687
<212> TYPE: PRT
<213> ORGANISM: Homo sapiens

<400> SEQUENCE: 10

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240
```

-continued

```
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
    290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
        355                 360                 365
Trp Leu Lys Asp Gly Leu Pro Ala Thr Glu Lys Ser Ala Arg Tyr Leu
    370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
        435                 440                 445
Arg Gln Ile Leu Thr Cys Thr Ala Tyr Gly Ile Pro Gln Pro Thr Ile
    450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
    530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
    610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
```

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685

<210> SEQ ID NO 11
<211> LENGTH: 57
<212> TYPE: DNA
<213> ORGANISM: Artificial sequence
<220> FEATURE:
<223> OTHER INFORMATION: RACE kit 3' oligonucleotide
<220> FEATURE:
<221> NAME/KEY: misc_feature
<222> LOCATION: (57)..(57)
<223> OTHER INFORMATION: n is a, c, g, or t

<400> SEQUENCE: 11
aagcagtggt atcaacgcag agtactttt tttttttttt tttttttttt tttttvn       57

<210> SEQ ID NO 12
<211> LENGTH: 20
<212> TYPE: DNA
<213> ORGANISM: Homo sapiens

<400> SEQUENCE: 12
cctcctgcga aacctcagtg                                                20

<210> SEQ ID NO 13
<211> LENGTH: 211
<212> TYPE: DNA
<213> ORGANISM: Artificial sequence
<220> FEATURE:
<223> OTHER INFORMATION: Intron 14 specific probe

<400> SEQUENCE: 13
aactgtatac atcaacgtca ccatcgtcat cgtcatcatc accattgtca tcatcatcat    60
catcgtcatc atcatcatca tcatagctat catcattatc atcatcatca tcatcatcat   120
catagctacc atttattgaa aactattatg tgtcaacttc aaagaactta tcctttagtt   180
ggagagccaa gacaatcata acaataacaa a                                  211

<210> SEQ ID NO 14
<211> LENGTH: 680
<212> TYPE: DNA
<213> ORGANISM: Artificial sequence
<220> FEATURE:
<223> OTHER INFORMATION: sFLT probe specific for both isoforms

<400> SEQUENCE: 14
tcaccatggt cagctactgg gacaccgggg tcctgctgtg cgcgctgctc agctgtctgc    60
ttctcacagg atctagttca ggttcaaaat taaaagatcc tgaactgagt ttaaaaggca   120
cccagcacat catgcaagca ggccagacac tgcatctcca atgcaggggg aagcagccc    180 ataaatggtc tttgcctgaa atggtgagta aggaaagcga aaggctgagc ataactaaat   240
ctgcctgtgg aagaaatggc aaacaattct gcagtacttt aaccttgaac acagctcaag   300
caaaccacac tggcttctac agctgcaaat atctagctgt acctacttca agaagaagg    360 aaacagaatc tgcaatctat atatttatta gtgatacagg tagacctttc gtagagatgt   420
acagtgaaat ccccgaaatt atacacatga ctgaaggaag ggagctcgtc attccctgcc   480
gggttacgtc acctaacatc actgttactt taaaaaagtt tccacttgac actttgatcc   540
ctgatggaaa acgcataatc tgggacagta gaaagggctt catcatatca aatgcaacgt   600

```
acaaagaaat agggcttctg acctgtgaag caacagtcaa tgggcatttg tataagacaa      660
actatctcac acatcgacaa                                                  680
```

<210> SEQ ID NO 15
<211> LENGTH: 14
<212> TYPE: PRT
<213> ORGANISM: Homo sapiens
<220> FEATURE:
<221> NAME/KEY: misc_feature
<223> OTHER INFORMATION: Antigenic bridging region

<400> SEQUENCE: 15

```
His Lys Ile Gln Gln Glu Pro Glu Leu Tyr Thr Ser Thr Ser
1               5                   10
```

<210> SEQ ID NO 16
<211> LENGTH: 1338
<212> TYPE: PRT
<213> ORGANISM: Homo sapiens
<220> FEATURE:
<221> NAME/KEY: misc_feature
<223> OTHER INFORMATION: Mass spec identified protein

<400> SEQUENCE: 16

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
```

```
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
        290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
        355                 360                 365
Trp Leu Lys Asp Gly Leu Pro Ala Thr Glu Lys Ser Ala Arg Tyr Leu
    370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
        435                 440                 445
Arg Gln Ile Leu Thr Cys Thr Ala Tyr Gly Ile Pro Gln Pro Thr Ile
    450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Ser Ile Leu Asp Ala Asp Ser
                485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
    530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
                565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
    610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
                645                 650                 655
Asp Gln Glu Ala Pro Tyr Leu Leu Arg Asn Leu Ser Asp His Thr Val
            660                 665                 670
Ala Ile Ser Ser Ser Thr Thr Leu Asp Cys His Ala Asn Gly Val Pro
        675                 680                 685
```

-continued

Glu Pro Gln Ile Thr Trp Phe Lys Asn Asn His Lys Ile Gln Gln Glu
690             695                 700

Pro Gly Ile Ile Leu Gly Pro Gly Ser Ser Thr Leu Phe Ile Glu Arg
705             710                 715                 720

Val Thr Glu Glu Asp Glu Gly Val Tyr His Cys Lys Ala Thr Asn Gln
            725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
            755                 760                 765

Ala Thr Leu Phe Trp Leu Leu Leu Thr Leu Phe Ile Arg Lys Met Lys
770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
                820                 825                 830

Leu Gly Arg Gly Ala Phe Gly Lys Val Val Gln Ala Ser Ala Phe Gly
            835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
            965                 970                 975

Leu Ser Asp Val Glu Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
            995                 1000                1005

Gly Met Glu Phe Leu Ser Ser Arg Lys Cys Ile His Arg Asp Leu
        1010                1015                1020

Ala Ala Arg Asn Ile Leu Leu Ser Glu Asn Asn Val Val Lys Ile
        1025                1030                1035

Cys Asp Phe Gly Leu Ala Arg Asp Ile Tyr Lys Asn Pro Asp Tyr
        1040                1045                1050

Val Arg Lys Gly Asp Thr Arg Leu Pro Leu Lys Trp Met Ala Pro
        1055                1060                1065

Glu Ser Ile Phe Asp Lys Ile Tyr Ser Thr Lys Ser Asp Val Trp
        1070                1075                1080

Ser Tyr Gly Val Leu Leu Trp Glu Ile Phe Ser Leu Gly Gly Ser
        1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe
    1190                1195                1200

Asn Ser Gly Ser Ser Asp Asp Val Arg Tyr Val Asn Ala Phe Lys
    1205                1210                1215

Phe Met Ser Leu Glu Arg Ile Lys Thr Phe Glu Glu Leu Leu Pro
    1220                1225                1230

Asn Ala Thr Ser Met Phe Asp Asp Tyr Gln Gly Asp Ser Ser Thr
    1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
    1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
    1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
    1325                1330                1335

<210> SEQ ID NO 17
<211> LENGTH: 16
<212> TYPE: PRT
<213> ORGANISM: Artificial sequence
<220> FEATURE:
<223> OTHER INFORMATION: Mass spec sequenced peptide
<220> FEATURE:
<221> NAME/KEY: misc_feature
<222> LOCATION: (434)..(449)
<223> OTHER INFORMATION: A portion identified by mass spec
<220> FEATURE:
<221> NAME/KEY: misc_feature
<222> LOCATION: (640)..(650)
<223> OTHER INFORMATION: A portion identified by mass spec
<220> FEATURE:
<221> NAME/KEY: misc_feature
<222> LOCATION: (657)..(665)
<223> OTHER INFORMATION: A portion identified by mass spec

<400> SEQUENCE: 17

Ala Val Ser Ser Phe Pro Asp Pro Ala Leu Tyr Pro Leu Gly Ser Arg
1               5                   10                  15

<210> SEQ ID NO 18
<211> LENGTH: 11
<212> TYPE: PRT
<213> ORGANISM: Artificial sequence
<220> FEATURE:

-continued

```
<223> OTHER INFORMATION: Mass spec sequenced peptide

<400> SEQUENCE: 18

Asn Val Tyr Thr Gly Glu Glu Ile Leu Gln Lys
1               5                   10

<210> SEQ ID NO 19
<211> LENGTH: 9
<212> TYPE: PRT
<213> ORGANISM: Artificial sequence
<220> FEATURE:
<223> OTHER INFORMATION: Mass spec sequenced peptide

<400> SEQUENCE: 19

Asp Gln Glu Ala Pro Tyr Leu Leu Arg
1               5
```

COMPOSITION FOR USE IN DETECTION OF SFLT-14

RELATED APPLICATIONS

This application is a division of U.S. patent application Ser. No. 13/685,892 filed on Nov. 27, 2012, which is a division of U.S. patent application Ser. No. 12/448,404 filed on Jan. 13, 2010, now abandoned, which is a National Phase of PCT Patent Application No. PCT/IL2007/001589 having International Filing Date of Dec. 20, 2007, which claims the benefit of priority under 35 USC §119(e) of U.S. Provisional Patent Application No. 60/875,822 filed on Dec. 20, 2006. The contents of the above applications are all incorporated by reference as if fully set forth herein in their entirety.

SEQUENCE LISTING STATEMENT

The ASCII file, entitled 59230SequenceListing.txt, created on Jun. 3, 2014, comprising 36,864 bytes, submitted concurrently with the filing of this application is incorporated herein by reference.

FIELD AND BACKGROUND OF THE INVENTION

The present invention, in some embodiments thereof, relates to isolated polypeptides and polynucleotides encoding same for the diagnosis and treatment of VEGF-associated medical conditions.

Vascular endothelial growth factor (VEGF), an endothelial specific mitogen, plays a key role in promoting both vasculogenesis and angiogenesis. VEGF plays an important regulatory function in the formation of new blood vessels during embryonic vasculogenesis and in angiogenesis during adult life.

The activities of VEGF are mediated primarily by its interaction with two high-affinity receptor tyrosine kinases: fms-like tyrosine kinase-1 (Flt-1/VEGFR-1) and kinase-insert domain region (KDR/Flk-1/VEGFR-2) both of which are expressed on vascular endothelial cell surfaces. Alternative splicing of Flt-1 results in the production of an endogenously secreted protein referred to as soluble Flt1 (sFlt1), which lacks the cytoplasmic and transmembrane domains but retains the ligand-binding domain [He et al., Mol. Endocrinol. (1999) 13: 537-545]. Thus, sFlt1 can antagonize circulating VEGF by binding it and preventing the interaction of VEGF with its endogenous receptors. sFlt1 also binds and antagonizes placental growth factor (PlGF), another member of the VEGF family, which is produced predominantly in the placenta, as well as of another VEGF family member known as VEGF-B.

VEGF is an important mediator of angiogenesis in a number of pathological conditions including tumor formation and metastasis of solid tumors. Numerous inhibitors of the VEGF/VEGF receptor pathway (e.g. monoclonal antibodies specific for VEGF) have been shown to prevent tumor growth via an antiangiogenic mechanism [Kim et al., Nature (1993) 362(6423):841-4].

Preeclampsia, the most common, dangerous, unpredictable complication of pregnancy is a major cause of maternal, fetal, and neonatal mortality worldwide. While the cause of preeclampsia remains unclear, the principle cause appears to be inadequate blood supply to the placenta making it release hormones or chemical agents that cause maternal endothelial dysfunction, alterations in metabolism and inflammation [Drife J O, Magowan (eds) Clinical Obstetrics and Gynecology, chapter 39, pp 367-370]. These consequently lead to hypertension association with proteinuria in the mother along with impaired placental blood flow, fetal growth restriction and consequential fetal oxidative stress.

During pregnancy, the major source of circulating sFlt1 is the placenta and only minor amounts are produced by other tissues (e.g. by endothelial cells and monocytes). Recent investigations have supported the finding that placental expression and serum levels of sFlt-1 are upregulated in preeclamptic pregnancies, in conjunction with decreased levels of circulating free VEGF and free PlGF, compared to normal pregnancies [Maynard et al., J. Clin. Invest. (2003) 111: 649-658]. The increase in sFlt1, followed by a decrease in free PlGF and free VEGF, was found to precede the onset of clinical disease by several weeks and appears to be more pronounced in severe and early onset preeclampsia [Levine et al., N. Engl. J. Med. (2004) 350: 672-683]. Postpartum, sFlt-1 levels decrease dramatically in both normal and preeclamptic pregnancies [Maynard et al., supra]. Thus, excess sFlt1, by neutralizing VEGF and PlGF, may play a crucial role in the pathogenesis of the maternal syndrome in preeclampsia.

Lam et al. [Lam et al, Hypertension (2005) 46(5): 1077-85] review the possibility of measuring circulating angiogenic proteins (e.g. PlGF) or anti-angiogenic proteins (e.g. sFlt-1) in the blood and urine of pregnant women as a diagnostic and screening tool for predicting preeclampsia. They have examined odds ratios, sensitivity and specificity for various sFlt-1 cutoff values in different trimesters. Lam et al. describe a strong correlation between high sFlt-1 levels and the risk and presence of preeclampsia. Furthermore, they have yielded the conclusion that the higher the sFlt-1 level, the more predictive it is of preeclampsia.

PCT Publication No. WO 2006/069373 discloses methods, compositions and kits for diagnosis of preeclampsia and hypertensive disorders in pregnancy. More specifically, WO 2006/069373 teaches assessment of preeclampsia or predisposition to preeclampsia by monitoring the levels of angiogenic factors, specifically VEGF, PlGF and sFlt-1, in urinary samples of pregnant women. WO 2006/069373 teaches that the higher the level of sFlt-1, the more predictive it is of preeclampsia. Furthermore, according to WO 2006/069373, preeclampsia is associated with a significant decrease in PlGF and significant increase in VEGF urine concentrations.

U.S. Publication No. 20050148040 discloses methods and compositions for screening of gestational disorders (e.g., gestational diabetes, preeclampsia and gestational hypertension) using specific biomarkers. The biomarkers taught are insulin resistance biomarkers [e.g., sex hormone binding globulin (SHBG)] and angiogenesis biomarkers including sFlt-1. More specifically, alterations in two pathways, insulin resistance (e.g., as evidenced by low serum levels of SHBG) and angiogenesis (e.g., as evidenced by low PlGF or high sFlt1), when combined can be used to predict gestational disorders.

U.S. Publication No. 20050025762 discloses methods for diagnosing and treating preeclampsia and eclampsia. U.S. Publication No. 20050025762 teaches treating or preventing preeclampsia and eclampsia using compounds that increase VEGF or PlGF levels (e.g., nicotine, adenosine), using compounds that decrease sFlt-1 levels (e.g., purified sFlt-1 antibody, an sFlt-1 antigen-binding fragment, small interfering RNAs, or double-stranded RNA) such as compounds that bind sFlt-1 and block growth factor binding (e.g., chemical compound, polypeptide, peptide, antibody).

SUMMARY OF THE INVENTION

According to an aspect of some embodiments of the present invention there is provided an isolated polypeptide comprising an amino acid sequence at least 70% homologous to SEQ ID NO: 4 as determined by protein BLAST algorithm.

According to some embodiments of the invention, the isolated polypeptide is capable of binding VEGF.

According to some embodiments of the invention, the isolated polypeptide is soluble.

According to some embodiments of the invention, the isolated polypeptide is as set forth in SEQ ID NO: 4.

According to some embodiments of the invention, the isolated polypeptide is as set forth in SEQ ID NO: 2.

According to some embodiments of the invention, the isolated polypeptide further comprises a heterologous amino acid sequence attached to the amino acid sequence.

According to some embodiments of the invention, the heterologous amino acid sequence is selected from the group consisting of an immunoglobulin, a galactosidase, a glucuronidase, a glutathione-S-transferase (GST), a carboxy terminal peptide (CTP) from chorionic gonadotrophin (CGβ), and a chloramphenicol acetyltransferase (CAT).

According to some embodiments of the invention, the isolated polypeptide is attached to a non-proteinaceous moiety.

According to some embodiments of the invention, the non-proteinaceous moiety is selected from the group consisting of polyethylene glycol (PEG), Polyvinyl pyrrolidone (PVP), poly(styrene comaleic anhydride) (SMA), and divinyl ether and maleic anhydride copolymer (DIVEMA).

According to an aspect of some embodiments of the present invention there is provided an isolated polynucleotide comprising a nucleic acid sequence encoding the isolated polypeptide, wherein the isolated polynucleotide is not genomic Flt1.

According to some embodiments of the invention, the isolated polynucleotide is an mRNA or a cDNA.

According to an aspect of some embodiments of the present invention there is provided an isolated polynucleotide as set forth in SEQ ID NO: 1 or 3.

According to an aspect of some embodiments of the present invention there is provided a nucleic acid construct comprising the nucleic acid sequence functionally attached to a cis-acting regulatory element.

According to an aspect of some embodiments of the present invention there is provided an isolated polynucleotide comprising a nucleic acid sequence capable of specifically hybridizing to the isolated polynucleotide and not to SEQ ID NO: 9.

According to an aspect of some embodiments of the present invention there is provided an isolated antibody comprising an antigen recognition domain which specifically binds the isolated polypeptide and not to SEQ ID NO: 10.

According to an aspect of some embodiments of the present invention there is provided a pharmaceutical composition comprising the isolated polypeptide and a pharmaceutically acceptable carrier.

According to an aspect of some embodiments of the present invention there is provided a pharmaceutical composition comprising the isolated polynucleotide and a pharmaceutically acceptable carrier.

According to an aspect of some embodiments of the present invention there is provided a pharmaceutical composition comprising the antibody and a pharmaceutically acceptable carrier.

According to an aspect of some embodiments of the present invention there is provided a pharmaceutical composition comprising the isolated polynucleotide and a pharmaceutically acceptable carrier.

According to an aspect of some embodiments of the present invention there is provided a use of an agent capable of regulating an activity and/or expression of sFlt-14 (SEQ ID NO: 1 or 2) and not sFlt-1 (SEQ ID NO: 9 or 10), for the manufacture of a medicament identified for treating a VEGF-associated medical condition.

According to some embodiments of the invention, the VEGF-associated medical condition is associated with reduced activity and/or expression of VEGF and whereas the regulating comprises downregulating the sFlt-14.

According to some embodiments of the invention, the VEGF-associated medical condition is associated with excessive activity and/or expression of VEGF and whereas the regulating comprises upregulating the sFlt-14.

According to some embodiments of the invention, the VEGF-associated medical condition is selected from the group consisting of preeclampsia, gestational diabetes, gestational hypertension, fetal growth restriction (FGR), fetal alcohol syndrome (FAS), cancer, corneal neovascularization and hypertension.

According to some embodiments of the invention, the agent comprises the antibody.

According to some embodiments of the invention, the agent comprises the isolated polynucleotide.

According to some embodiments of the invention, the agent comprises the isolated polypeptide.

According to some embodiments of the invention, the agent comprises the isolated polynucleotide.

According to an aspect of some embodiments of the present invention there is provided a method of detecting sFlt-14 (SEQ ID NO: 2) in a biological sample, the method comprising: (a) contacting the biological sample with the antibody such that the sFlt-14 and the antibody form a complex; and (b) measuring a presence or a level of the complex to thereby detect sFlt-14 in the biological sample.

According to an aspect of some embodiments of the present invention there is provided a method of detecting sFlt-14 (SEQ ID NO: 1) in a biological sample, the method comprising: (a) contacting the biological sample with the isolated polynucleotide so as to form a hybridization complex; and (b) measuring a presence or a level of the complex to thereby detect sFlt-14 in the biological sample.

According to some embodiments of the invention, the measuring is effected by a method selected from the group consisting of PCR, Real Time PCR, RT PCR, nucleic acid sequence-based amplification (NASBA), Northern blot and in situ hybridization.

According to an aspect of some embodiments of the present invention there is provided a method of diagnosing a pregnancy-associated medical condition associated with maternal or fetal stress in a subject in need thereof, the method comprising detecting expression level of sFlt-14 (SEQ ID NO: 1 or 2) in a biological sample of the subject using an agent capable of recognizing sFlt-14 (SEQ ID NO: 1 or 2) and not sFlt-1 (SEQ ID NO: 9 or 10), wherein an expression level of the sFlt-14 above a predetermined threshold is indicative of the pregnancy-associated medical condition associated with maternal or fetal stress.

According to an aspect of some embodiments of the present invention there is provided a method of diagnosing a pregnancy-associated medical condition associated with maternal or fetal stress in a subject in need thereof, the method comprising detecting expression level of sFlt-14 (SEQ ID NO: 1 or 2) in a biological sample, wherein the biological sample is of a gestation week 13 and on, and wherein an expression level of the sFlt-14 above a predetermined threshold is indicative of the pregnancy-associated medical condition associated with maternal or fetal stress.

According to some embodiments of the invention, the condition is selected from the group consisting of preeclampsia, gestational diabetes, gestational hypertension, fetal growth restriction (FGR), and fetal alcohol syndrome (FAS).

According to some embodiments of the invention, the biological sample is selected from the group consisting of a urine sample, a blood sample, a serum sample, a placenta biopsy, a chorionic villus sample, and an amniotic fluid sample.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
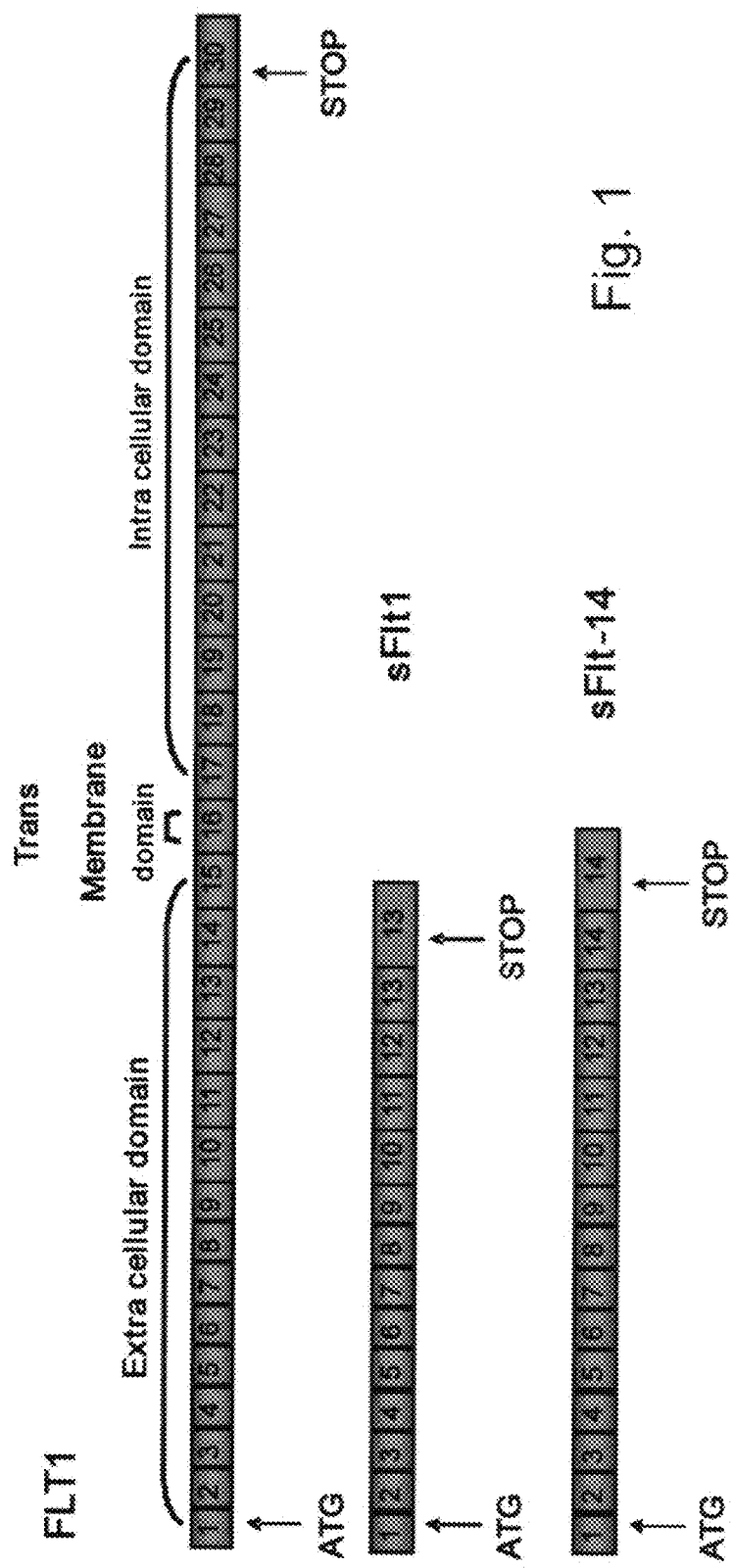

FIG. 1 is a schematic representation of the FLT1-full transmembrane receptor (top), the well-known soluble sFlt1 variant (middle), and the novel sFlt-14 variant of the present invention (bottom). Arrows mark the beginning of translation (ATG) and the stop (STOP) points. Exons are indicated by the dark numbered boxes and introns 13 and 14 are indicated by the light numbered boxes.

FIG. 2A depicts the unique cDNA sequence of the novel sFlt-14 isoform. The sequence was cloned by 3' RACE from a human preeclamptic placenta. The shown sequence starts near the beginning of exon 14 and ends with a poly A tail. The italic letters represent the coding region that is derived from exon 14 and intron 14. The stop codon is in bold. The underlined sequence is an Alu repeat nested in the 3' UTR.

Figure 2B:
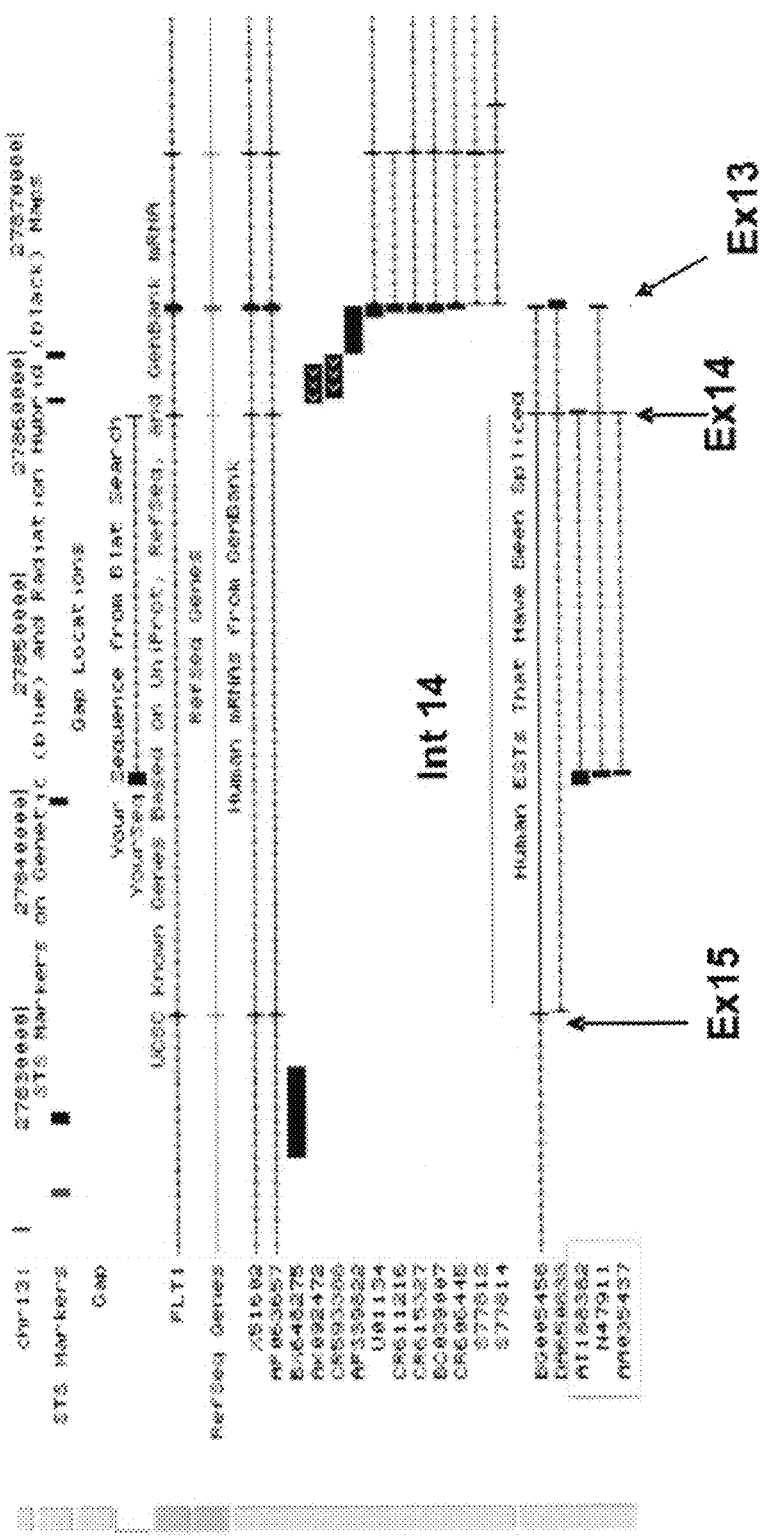

FIG. 2B depicts a window taken from the UCSC genome browser after a blast search with the sequence that appears above (FIG. 2A). The search located three ESTs with a similar splicing pattern to the one found in the above sequence: AI188382, N47911 and AA035437.

FIG. 3A depicts the amino acid sequence of sFlt-14 as deduced from its mRNA. The original reading frame was kept, starting with the known translation start point of sFlt-1 and transmembrane Flt. The amino acids shared with the full transmembrane receptor (but not with sFlt-1) are underlined. The unique 28 amino acids found only in the variant sFlt-14 of the invention (from intron 14) are depicted in bold.

FIG. 3B depicts sequences of peptides synthesized in order to create specific polyclonal antibodies which distinguish between sFlt-1 and sFlt-14. Of note, whereas CESS is unique to sFlt-14, CHFK can distinguish between the alternatively-spliced isoforms only in conjunction with analysis of the protein size.

FIGS. 4A-B are pictures depicting the relative abundance of the full membrane receptor Flt, sFlt-1 (also designated sFlt-13) and the novel sFlt-14 in different cell types. FIG. 4A shows the expression of the full receptor Flt and its two alternatively-spliced variants sFlt-1 and sFlt-14 in endothelial cells (left column), normal placentae (middle column) and preeclampsia placentae (right column). RNA blots were hybridized with a probe detecting an extracellular sequence common to all three (each yields a band of equal intensity, irrespective of size). Of note, endothelial cells preferentially produce the full receptor and sFlt1, whereas placentae predominantly produce sFlt-14. However, a dramatic upregulation of sFlt-14 is exhibited in preeclampsia placentae; FIG. 4B shows the expression of sFlt-1 and sFlt-14 in Primary cultures of endothelial cells (EC) and in vascular smooth muscle cells (VSMC) isolated from a human saphena vein. Of note, sFlt1 and sFlt-14 are exclusively expressed by ECs and VSMCs, respectively. The bottom panels of FIGS. 4A-B represent 28S and 18S RNA expression that was used as a loading control.

FIGS. 5A-D are pictures depicting sFlt-14 mRNA and protein expression in the context of the preeclamptic placenta. FIGS. 5A-B show immunohistochemical detection of the sFlt-14 protein using the specific CESS antibody; FIGS. 5C-D show in-situ hybridization with a sFlt-14-specific probe (derived from intron 14) identifying sFlt-14-expressing cells. Of note, massive expression of sFlt-14 mRNA and protein in syncytial knots of the preeclamptic placenta.

FIG. 6 is a western immunoblot image depicting immunoprecipitation of the sFlt-14 protein in normal term placentae with a CESS antibody or with a Flt1 antibody.

FIG. 7 shows a mass-spectrometry identification of sFlt-14 (SEQ ID NOs: 16-19).

Figure 8:
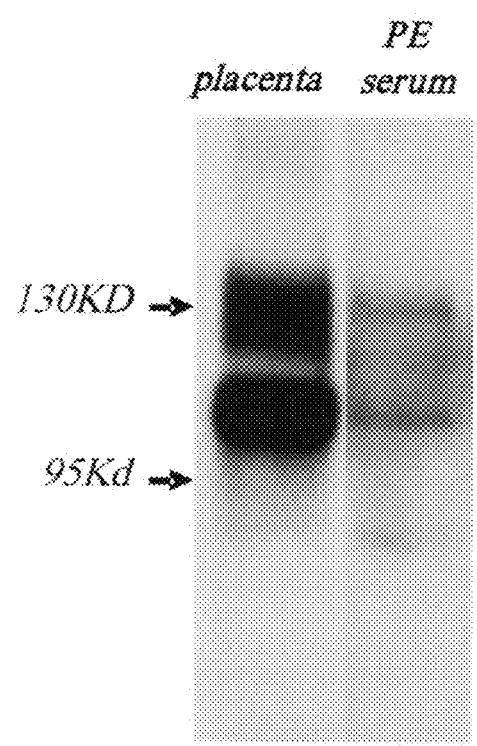

FIG. 8 is a western immunoblot image depicting expression levels of sFlt-14 proteins in serum and placentae samples of preeclamptic subjects. Protein detection was carried out using a specific sFlt-14 antibody (CESS, directed against SEQ ID NO: 5).

Figure 9A:
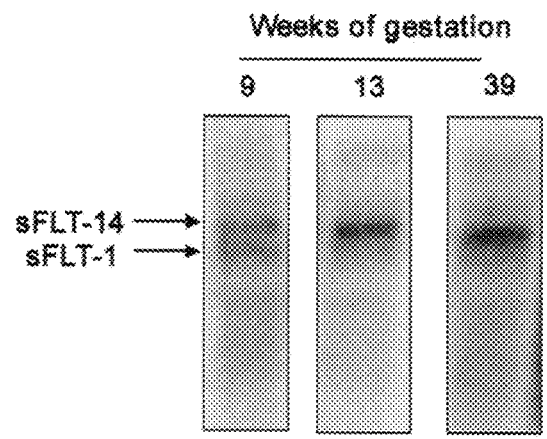
Figure 9B:
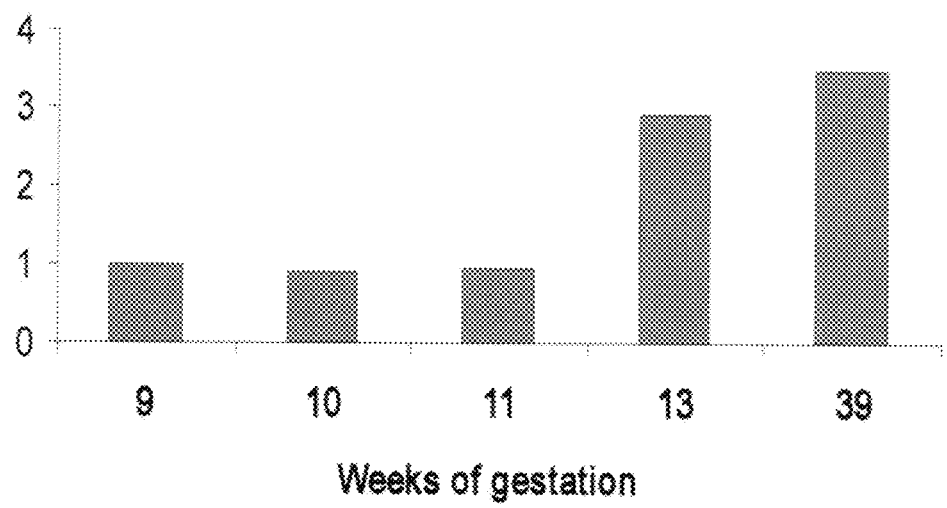

FIGS. 9A-B depict characterization of sFlt proteins during the course of pregnancy. FIG. 9A illustrates RNA expression of sFlt-1 and sFlt-14 during different time points of normal gestation; and FIG. 9B shows quantification of the ratio of the two sFlt1 isoforms (sFlt-1 and sFlt-14) during different time points of normal gestation: weeks 9-11, week 13, and week 39.

Figure 10A:
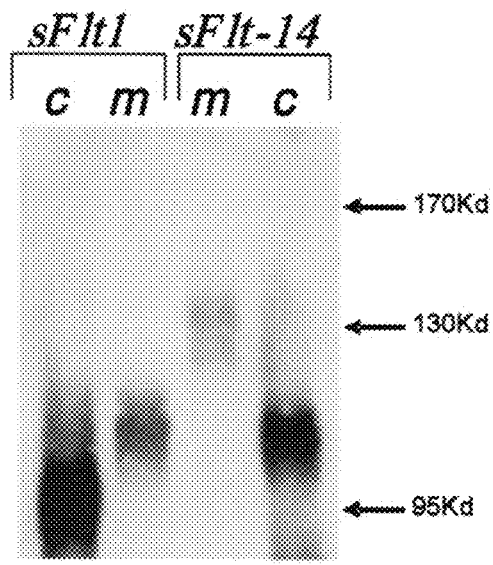
Figure 10B:
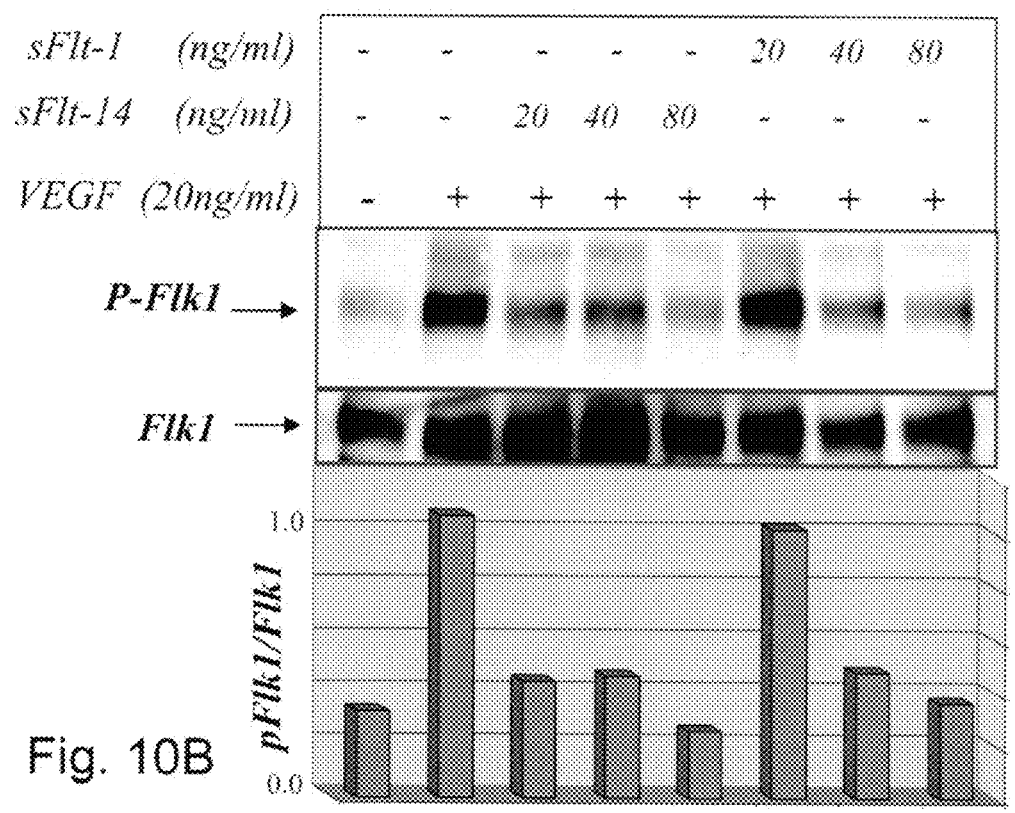

FIGS. 10A-B depict sFlt-14 as a VEGF receptor. FIG. 10A shows recombinant sFlt-14 and sFlt-1 proteins from the cellular fraction (c) or from the media (m). sFlt-14 is located at 115 Kd and 130 Kd, in the cellular fraction and media, respectively. sFlt-1 is located at 100 Kd and 120 Kd, in the cellular fraction and media, respectively; and FIG. 10B shows a VEGF inhibition assay where VEGF was preincubated with sFlt-1 or sFlt-14 prior to addition of VEGF-R2 (by addition of growth medium of Porcine Aortic Endothelial cells). VEGF-R2 phosphorylation levels were measured as a function of added sFlt-14/VEGF ratio or sFlt-1/VEGF ratio. Of note, nearly complete inhibition of VEGF-R2 phosphorylation was evident already at a 1:1 sFlt-14/VEGF ratio.

Figure 11A:
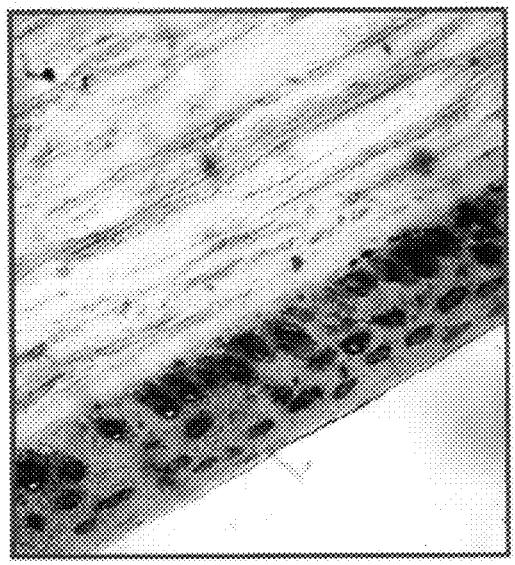
Figure 11B:

FIGS. 11A-B depict sFlt-14 expression in human cornea sections. FIG. 11A shows immunohistochemistry of sFlt-14 using a specific antibody (CESS directed against SEQ ID NO: 5); and FIG. 11B shows control immunohistochemistry using a pre immuned serum. Of note, sFlt-14 was readily seen in the corneal epithelia.

DESCRIPTION OF EMBODIMENTS OF THE INVENTION

The present invention, in some embodiments thereof, relates to isolated polypeptides and polynucleotides encoding same for the diagnosis and treatment of VEGF-associated medical conditions.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The soluble VEGF receptor sFlt-1, which specifically binds and antagonizes circulating VEGF and PlGF, has been previously contemplated as the leading cause of preeclampsia and as such was suggested as a marker of and target for treating this condition [Maynard et al., supra; Levine et al., supra]. These findings were based on the use of clinical tools such as antibodies and oligonucleotides directed to sequences shared by the soluble and non-soluble VEGF receptors.

While reducing some embodiments of the present invention to practice, the present inventors have identified a novel VEGF receptor variant. This variant is soluble, secreted, comprises a unique amino acid sequence (SEQ ID NO: 4) and is expressed during preeclampsia. Using antibodies or oligonucleotides specifically directed to the unique sequence (SEQ ID NOs 4 or 3) of sFlt-14, the present inventors were able to show that it is the sFlt-14 rather than sFlt-1 (supra) that is highly expressed in preeclampsia. These results prove beyond any doubt the clinical value of sFlt-14.

As is illustrated in the Examples section which follows, the novel sFlt-14 (SEQ ID NOs: 1 and 2) of the present invention differs from the full transmembrane receptor Flt1 and from the known sFlt1 by comprising a unique 28 amino acid sequence (SEQ ID NO: 4, see Example 1 and FIG. 1) derived by readthrough of intron 14. This novel sFlt-14 receptor is expressed in placentae and is highly upregulated in preeclamptic placentae (see Example 3 and FIG. 4A). Moreover, the results presented herein illustrate that trophoblastic cells within the syncytial knots produce sFlt-14 (Example 4 and FIGS. 5A-D). Thus, sFlt-14 provides a valuable indicator of preeclampsia or predisposition thereof. Furthermore, since sFlt-14 functions in antagonizing VEGFR ligands (e.g., VEGF), modulating sFlt-14 levels (e.g. downregulating or upregulating) may serve as a powerful tool in treatment of VEGF associated conditions (hyper angiogenesis e.g., cancer and neovascularized cornea).

Thus, according to one aspect of the present invention there is provided an isolated polynucleotide comprising a nucleic acid sequence encoding a polypeptide comprising an amino acid sequence at least about 50%, at least about 55%, at least about 60%, at least about 65%, at least about 70%, at least about 75%, at least about 80%, at least about 85%, at least about 87%, at least about 89%, at least about 90%, at least about 91%, at least about 93%, at least about 95% or more say 100% identical or homologous to SEQ ID NO: 4, wherein the isolated polynucleotide is not genomic Flt1.

As used herein the phrase "an isolated polynucleotide" refers to a single or double stranded nucleic acid sequences which is isolated and provided in the form of an RNA sequence, a complementary polynucleotide sequence (Cdna) and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "composite polynucleotide sequence" refers to a sequence, which is at least partially complementary and partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements (further explained in detail hereinbelow).

According to an exemplary embodiment of this aspect of the present invention the isolated polypeptide encoded by the polynucleotide described herein is capable of binding a VEGFR ligand. Examples of such ligands include, without limitation, VEGF (VEGF-A, GeneBank Accession No. NP_001020537), VEGF-B (GeneBank Accession No. NP_003368) and Placenta growth factor (PlGF, GeneBank Accession No. NP_002623).

According to an exemplary embodiment, binding of the polypeptide is expected to be in a range of about $10^{-9}$ M-$10^{-12}$ M.

According to an exemplary embodiment of this aspect of the present invention, the isolated polynucleotide is as set forth in SEQ ID NO: 1. Of note, it is suggested that naturally occurring forms of the polynucleotide sequences of some embodiments of the present invention are splice variants of the genomic Flt1. Examples of genomic Flt1 are depicted in GeneBank Accession No. NC_000013.9 region: complement (27773790 to 27967232) GI:51511729 for human genomic Flt1 and GeneBank Accession No. NC_006480.2 region: complement (27975879 to 28168596) GI:114795054 for chimpanzee genomic Flt1 (see FIG. 1 showing exon/intron organization).

The phrase "splice variant", as used herein, refers to alternative forms of RNA transcribed from a VEGF receptor gene. Splice variation arises naturally through use of alternative splicing sites within a transcribed RNA molecule, or less commonly between separately transcribed RNA molecules, and may result in several different mRNAs transcribed from the same gene. Splice variants may encode polypeptides having altered amino acid sequence due to intron inclusion, exon exclusion or a combination of both. The term splice variant is also used herein to denote a polypeptide encoded by a splice variant of an mRNA transcribed from a gene.

According to an alternative embodiment the isolated polynucleotide of the present invention is as set forth in SEQ ID NO: 3.

It will be appreciated that homologues of the sequences described hereinabove are also envisaged by the present invention. Accordingly, the polynucleotide of this aspect of the present invention may have a nucleic acid sequence at least about 50%, at least about 55%, at least about 60%, at least about 65%, at least about 70%, at least about 75%, at least about 80%, at least about 85%, at least about 87%, at least about 89%, at least about 90%, at least about 91%, at least about 93%, at least about 95% or more say 100% identical or homologous to SEQ ID NO: 1 or 3, as determined using BlastN software of the National Center of Biotechnology Information (NCBI) using default parameters.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the polynucleotide sequences of the present invention encode previously unidentified polypeptides, the present invention also encompasses novel polypeptides or portions thereof, which are encoded by the isolated polynucleotides and respective nucleic acid fragments thereof described hereinabove.

Thus, according to another aspect of the present invention there is provided an isolated polypeptide comprising an amino acid sequence at least about 50%, at least about 55%, at least about 60%, at least about 65%, at least about 70%, at least about 75%, at least about 80%, at least about 85%, at least about 87%, at least about 89%, at least about 90% at least about 91%, at least about 93%, at least about 95% or more say 100% homologous to SEQ ID NO: 4 as determined by protein BLAST algorithm.

In an exemplary embodiment the isolated polypeptide is as set forth in SEQ ID NO: 2 or 4.

The present invention also encompasses fragments (e.g., as short as a specific antigenic determinant e.g., at least about 6, at least about 8, at least about 10 at least about 20 amino acids such as derived from SEQ ID NO: 4) of the above described polypeptides and polypeptides having mutations, such as deletions, insertions or substitutions of one or more amino acids, either naturally occurring or man induced, either randomly or in a targeted fashion. These fragments may be used to elicit antibody production against the isolated polypeptides of the invention.

As used herein the phrase "an isolated polypeptide" refers to isolated, native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, including but not limited to $CH_2$—NH, $CH_2$—S, $CH_2$—S=O, O=C—NH, $CH_2$—O, $CH_2$—$CH_2$, S=C—NH, CH=CH, and CF=CH; backbone modifications; and residue modifications. Methods for preparing peptidomimetic compounds are well known in the art and are specified, for example, in Ramsden, C. A., ed. (1992), Quantitative Drug Design, Chapter 17.2, F. Choplin Pergamon Press, which is incorporated by reference as if fully set forth herein. Further details in this respect are provided hereinbelow.

Peptide bonds (—CO—NH—) within the peptide may be substituted, for example, by N-methylated bonds (—N(CH3)-CO—); ester bonds (—C(R)H—C—O—O—C(R)—N—); ketomethylene bonds (—CO—CH2-); α-aza bonds (—NH—N(R)—CO—), wherein R is any alkyl group, e.g., methyl; carba bonds (—$CH_2$—NH—); hydroxyethylene bonds (—CH(OH)—CH2-); thioamide bonds (—CS—NH—); olefinic double bonds (—CH=CH—); retro amide bonds (—NH—CO—); and peptide derivatives (—N(R)—CH2-CO—), wherein R is the "normal" side chain, naturally presented on the carbon atom. These modifications can occur at any of the bonds along the peptide chain and even at several (2-3) at the same time.

Natural aromatic amino acids, Trp, Tyr, and Phe, may be substituted for synthetic non-natural acids such as, for instance, tetrahydroisoquinoline-3-carboxylic acid (TIC), naphthylelanine (Nol), ring-methylated derivatives of Phe, halogenated derivatives of Phe, and o-methyl-Tyr.

In addition to the above, the polypeptides of the present invention may also include one or more modified amino acids or one or more non-amino acid monomers (e.g., fatty acids, complex carbohydrates, etc.).

The term "amino acid" or "amino acids" is understood to include the 20 naturally occurring amino acids; those amino acids often modified post-translationally in vivo, including, for example, hydroxyproline, phosphoserine, and phosphothreonine; and other less common amino acids, including but not limited to 2-aminoadipic acid, hydroxylysine, isodesmosine, nor-valine, nor-leucine, and ornithine. Furthermore, the term "amino acid" includes both D- and L-amino acids.

Thus, polypeptides of the present invention can be of a short length typically 5-10, 10-20, 20-50, 50-100 amino acids in length and longer e.g., 100-200, 200-300, 300-400, 400-500, 500-600, 600-733 amino acids in length.

Mimetic technology may be used to generate peptides which are engineered to have at least one modified feature as compared to the naturally occurring polypeptide (e.g., SEQ ID NO: 2) while maintaining a biological activity of interest e.g., VEGF binding, antibody binding and the like.

Generation of peptide mimetics can be effected using various approaches which are well known in the art, including, for example, display techniques.

Thus, the present invention contemplates a display library comprising a plurality of display vehicles (such as phages, viruses or bacteria) each displaying at least 5, at least 7, at least 11, at least 15, at least 20, at least 25 consecutive amino acids derived from the isolated polypeptide sequence of sFlt-14 (e.g., SEQ ID NO: 2 and SEQ ID NO: 4).

Peptide mimetics can also be uncovered using computational biology.

According to an embodiment of the present invention, the isolated polypeptides are soluble.

As used herein the term "soluble" refers to the ability of the molecules of the present invention to dissolve in a physiological aqueous solution (pH about 7, e.g., solubility level in aqueous media of >100 μg/ml) without substantial aggregation. Thus, it is readily understood that soluble sFlt-14 are preferably devoid of hydrophobic transmembrane domains.

Being soluble, the polypeptides of the present invention may be secreted. As depicted in the Example section which follows, the present inventors have revealed, for the first time, that sFlt-14 (and not sFlt-1) is the soluble receptor found in the serum of preeclamptic subjects (Example 7 and FIG. 8). Thus, sFlt-14 is the major VEGF receptor in the circulation of preeclamptic subjects.

The peptides of the present invention are preferably utilized in a linear form, although it will be appreciated that in cases where cyclization does not severely interfere with peptide characteristics, cyclic forms of the peptide can also be utilized.

The peptides of the present invention may be synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York).

In general, peptide synthesis methods comprise the sequential addition of one or more amino acids or suitably protected amino acids to a growing peptide chain. Normally, either the amino or the carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth; traditionally this process is accompanied by wash steps as well. After all of the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide, and so forth.

Further description of peptide synthesis is disclosed in U.S. Pat. No. 6,472,505. A preferred method of preparing the peptide compounds of the present invention involves solid-phase peptide synthesis, utilizing a solid support. Large-scale peptide synthesis is described by Andersson Biopolymers 2000, 55(3), 227-50.

In cases where large amounts of the peptides of the present invention are desired, the polypeptides of the present invention can be generated using recombinant techniques such as described by Bitter et al. (1987) Methods in Enzymol. 153:516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988, Methods for Plant Molecular Biology, Academic Press, NY, Section VIII, pp 421-463.

Briefly, an expression construct (i.e., expression vector), which includes the isolated polynucleotide of the present invention (e.g., SEQ ID NO: 1, 3), optionally in frame fused to a nucleic acid sequence encoding a heterologous amino acid sequence (e g immunoglobulin sequence, as further described hereinbelow), positioned under the transcriptional control of a regulatory element, such as a promoter (as explained in detail hereinbelow), is introduced into host cells.

For expression in mammalian cells, pRK5-based vectors [Schall et al., Cell, 61:361-370 (1990)]; and CDM8-based vectors [Seed, Nature, 329:840 (1989)] can be used.

Methods of introducing the expression construct into a host cell are well known in the art and include electroporation, lipofection and chemical transformation (e.g., calcium phosphate).

The "transformed" cells are cultured under suitable conditions, which allow the expression of the polypeptide encoded by the nucleic acid sequence.

Following a predetermined time period, the expressed chimeric molecule is recovered from the cell or cell culture, and purification is effected according to the end use of the recombinant polypeptide.

Depending on the host/vector system utilized, any of a number of suitable transcription and translation elements including constitutive and inducible promoters, transcription enhancer elements, transcription terminators, and the like, can be used in the expression vector [see, e.g., Bitter et al., (1987) Methods in Enzymol. 153:516-544].

Other than containing the necessary elements for the transcription and translation of the inserted coding sequence (encoding the chimera), the expression construct of the present invention can also include sequences engineered to optimize stability, production, purification, yield or toxicity of the expressed fusion protein.

A variety of prokaryotic or eukaryotic cells can be used as host-expression systems to express the fusion protein coding sequence. These include, but are not limited to, microorganisms, such as bacteria transformed with a recombinant bacteriophage DNA, plasmid DNA or cosmid DNA expression vector containing the chimera coding sequence; yeast transformed with recombinant yeast expression vectors containing the chimera coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the chimera coding sequence. Mammalian expression systems are preferably used to express the chimera of the present invention.

The choice of host cell line for the expression of the molecules depends mainly on the expression vector. Eukaryotic expression systems are preferred (e.g., mammalian and insects) since they allow post translational modifications (e.g., glycosylation). Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient expression. CDM8-based vectors can be used to transfect COS cells by the DEAE-dextran method (Aruffo et al., Cell, 61:1303-1313 (1990); Zettmeissl et al., DNA Cell Biol. US, 9:347-353 (1990)]. If larger amounts of protein are desired, the molecules can be expressed after stable transfection of a host cell line. It will be appreciated that the presence of a hydrophobic leader sequence at the N-terminus of the molecule will ensure processing and secretion of the molecule by the transfected cells.

It will be appreciated that the use of bacterial or yeast host systems may be preferable to reduce cost of production. However since bacterial host systems are devoid of protein glycosylation mechanisms, a post production glycosylation may be needed.

In any case, transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant chimera molecule of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant protein is effected.

Molecules of the present invention are preferably retrieved in "substantially pure" form. As used herein, "substantially pure" refers to a purity that allows for the effective use of the protein in the applications, described hereinbelow.

As mentioned, the isolated polypeptide of this aspect of the present invention may further comprise a heterologous amino acid sequence.

As used herein the phrase "heterologous amino acid sequence" refers to an amino acid sequence which does not form a part of a naturally occurring sFlt-14 (e.g., SEQ ID NO: 2) amino acid sequence. This sequence preferably confers solubility to the molecule of this embodiment of the present invention, and preferably increases the half-life of the chimeric molecule in the serum.

The heterologous amino acid sequence is generally localized at the amino- or carboxyl-terminus of the isolated polypeptide of the present invention.

One or more heterologous amino acid sequences can be conjugated to the sFlt-14 amino acid sequence of the present invention. Examples of heterologous amino acid sequences commonly used in fusion protein construction include, but are not limited to, immunoglobulin, galactosidase, glucuronidase, glutathione-S-transferase (GST), carboxy terminal peptide (CTP) from chorionic gonadotrophin (CGβ) and chloramphenicol acetyltransferase (CAT).

The exact site at which fusion (conjugation) between the heterologous sequence and the sFlt-14 amino acid sequence is not critical and the optimal site can be determined by routine experimentation as long as functionality of the polypeptide is maintained (e.g., VEGF binding). Methods of ligand binding assessment are well known in the art (e.g., using a radiolabeled ligand in a binding assay, or an ELISA).

Additionally or alternatively as mentioned hereinabove the isolated polypeptide of the present invention may be attached to a non-proteinaceous moiety.

Thus, embodiments of the present invention provide an isolated polypeptide or polynucleotide being attached to a non-proteinaceous moiety.

Such a conjugate molecule is highly stable (resistant to in-vivo proteolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation).

The phrase "non-proteinaceous moiety" as used herein refers to a molecule not including peptide bonded amino acids that is attached to the above-described sFlt-14 amino acid sequence. According to an embodiment the non-proteinaceous moiety of this aspect of the present invention is a polymer or a co-polymer (synthetic or natural). Non-limiting examples of the non-proteinaceous moiety of the present invention include polyethylene glycol (PEG), Polyvinyl pyrrolidone (PVP), divinyl ether and maleic anhydride copolymer (DIVEMA; see for example, Kaneda Y, et al., 1997, Biochem. Biophys. Res. Commun. 239: 160-5) and poly(styrene comaleic anhydride) (SMA; see for example, Mu Y, et al., 1999, Biochem Biophys Res Commun. 255: 75-9).

Conjugation of such a non-proteinaceous moiety confers the polypeptide of this aspect of the present invention with stability (e.g., against protease activities) and/or solubility (e.g., within a biological fluid such as blood, digestive fluid) while preserving its biological activity and prolonging its half-life. Such a conjugation is advantageous particularly in cases of therapeutic proteins which exhibit short half-life and rapid clearance from the blood. The increased half-lives of conjugated proteins, in the plasma, results from increased size of protein conjugates (which limits their glomerular filtration) and decreased proteolysis due to polymer steric hindrance. Generally, the more polymer chains attached per peptide, the greater the extension of half-life. However, measures are taken not to reduce the specific activity of the sFlt-14 amino acid sequence of the present invention (e.g., sFlt-14 binding to VEGF). Methods of conjugating non-protein moieties to amino acid sequences are well known in the art (as described in, for example, Veronese F M, Biomaterials, Volume 22(5), 2001, pp. 405-417(13), Elsevier Publishing; and Haruhiko Kamada, et al., 2000, Cancer Research 60: 6416-6420, which are fully incorporated herein by reference).

Thus, the present inventors have uncovered a novel soluble and secreted variant of VEGFR. This variant is expressed in serum and placentae of preeclamptic subjects and as such detection of same may be clinically valuable such as in the diagnosis of preeclampsia.

Thus, according to some embodiments of yet another aspect of the present invention there is provided a method of detecting sFlt-14 (e.g., SEQ ID NO: 2) in a biological sample (including in vivo detection).

Typically, the method is effected by determining sFlt-14 level, presence or ratio (such as with respect to other Flt-1 isoforms, e.g., sFlt-1 as shown in FIG. 9B).

In accordance with some embodiments of this aspect of the present invention the methods comprising, contacting the biological sample with an antibody comprising an antigen recognition domain which specifically binds the isolated polypeptide of sFlt-14 (e.g., SEQ ID NO: 2) and not to SEQ ID NO: 10 such that the sFlt-14 and the antibody form a complex; and measuring a presence or a level of the complex to thereby detect sFlt-14 in the biological sample.

As used herein a "biological sample" refers to a biological material, such as cells, tissues (e.g., placenta, chorionic villus sample, solid tumor) and fluids such as amniotic fluid, blood, serum, plasma, lymph, bile fluid, urine, saliva, sputum, synovial fluid, semen, tears, cerebrospinal fluid, bronchioalveolar large fluid, ascites fluid, pus, conditioned medium and the like in which sFlt-14 may be present. The biological sample is a maternal or fetal sample. The biological sample, may be ex vivo or in vitro analyzed, but can also be analyzed without retrieval from the subject's body.

As shown in Example 8 and in FIGS. 9A-B (in the Examples section which follows), sFlt-14 is exclusively expressed from week 13 of gestation. Thus, when analysis of sFlt-14 level or presence is effected prior to this week, specific antibodies or oligonucleotides are preferably employed. From week 13 and on, the use of antibodies or oligonucleotides directed at common sequence regions of Flt-1 variants may also be contemplated.

Thus, antibodies of some embodiments of this aspect of the present invention may be directed to the amino acid sequence CELYTSTSPSSSSSS (SEQ ID NO: 5). This peptide comprises amino acids derived from the unique 28 amino acid sequence of sFlt-14 (SEQ ID NO: 4) which are not present in other Flt polypeptides (i.e. in the transmembrane and soluble sFlt-1), as depicted in SEQ ID NO: 10. Alternatively, antibodies may be directed to the amino acid sequence CHANGVPEPQITWFK (SEQ ID NO: 6). This peptide comprises amino acids derived from an amino acid sequence shared by sFlt-14 and the transmembrane Flt-1, but not by the sFlt-1 (SEQ ID NO: 10). Conversely, antibodies may be directed to the bridging region which comprises both the common amino acid sequence and the unique amino acid sequence. An exemplary bridging region which antibodies can be directed to is HKIQQEPELYTSTS (SEQ ID NO: 15). Measures are taken to select antibodies which are specific to sFlt-14 and not Flt-1 or its soluble form.

Specific peptides chosen for antibody generation are preferably selected immunogenic (i.e., capable of stimulating an antibody response). Parameters for testing peptide immunogenicity are well known in the art including, but not limited to, foreigness, molecular size, chemical composition and heterogeneity and susceptibility to antigen processing and presentation. Various sequence analysis software applications are known in the art, which provide an immunogenicity index according to, for example, the Jameson-Wolf algorithm. Examples include, but are not limited to, Sciprot (available from wwwdotasiaonlinedotnetdothk/~twcbio/DOCS/1/scPrteindothtm) and Macvector (available from wwwdotaccelrysdotcom/products/macvector/) as well as the widely utilized GCG package (Genetics Computer Group, Wisconsin).

The term "antibody" as used herein includes whole antibody molecules as well as functional fragments thereof, such as Fab, F(ab')$_2$, and Fv that are capable of binding with antigenic portions of the target polypeptide. These functional antibody fragments constitute preferred embodiments of the present invention, and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule as described in, for example, U.S. Pat. No. 4,946,778.

Methods of generating such antibody fragments are well known in the art (See for example, Harlow and Lane, Antibodies: A Laboratory Manual, Cold Spring Harbor Laboratory, New York, 1988, incorporated herein by reference).

Purification of serum immunoglobulin antibodies (polyclonal antisera) or reactive portions thereof can be accomplished by a variety of methods known to those of skill in the art including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes include IgD, IgE, IgA, IgM and related proteins.

Methods for the generation and selection of monoclonal antibodies are well known in the art, as summarized for example in reviews such as Tramontano and Schloeder, Methods in Enzymology 178, 551-568, 1989. A sFlt-14 polypeptide (or fragment thereof) of the present invention may be used to generate antibodies in vitro. More preferably, the sFlt-14 polypeptide of the present invention is used to elicit antibodies in vivo. In general, a suitable host animal is immunized with the sFlt-14 polypeptide of the present invention. Advantageously, the animal host used is a mouse of an inbred strain. Animals are typically immunized with a mixture comprising a solution of the sFlt-14 polypeptide of the present invention in a physiologically acceptable vehicle, and any suitable adjuvant, which achieves an enhanced immune response to the immunogen. By way of example, the primary immunization conveniently may be accomplished with a mixture of a solution of the sFlt-14 polypeptide of the present invention and Freund's complete adjuvant, the mixture being prepared in the form of a water in oil emulsion. Typically the immunization will be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the sFlt-14 polypeptide can be determined during the immunization schedule by any convenient method including by way of example radioimmunoassay, or enzyme linked immunosorbant assay, which is known as the ELISA assay. When suitable antibody titers are achieved, antibody-producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multi-well plates, and the culture supernatants are screened to identify cultures containing antibodies that recognize the hapten of choice. Hybridomas that secrete antibodies that recognize the sFlt-14 polypeptides of the present invention are cloned by limiting dilution and expanded, under appropriate culture conditions. Monoclonal antibodies are purified and characterized in terms of immunoglobulin type and binding affinity.

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, in U.S. Pat. Nos. 4,036,945 and 4,331,647, and references contained therein, which patents are hereby incorporated by reference in their entirety (see also Porter, R. R., Biochem. J., 73: 119-126, 1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al. (Proc. Nat'l Acad. Sci. USA 69:2659-62, 1972). Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, all of which are hereby incorporated, by reference, in entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick and Fry Methods, 2: 106-10, 1991).

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source, which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human monoclonal antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992);

Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Thus the antibodies may be contacted with the biological sample so at to form an immunocomplex. Detection of the level and presence of the complex may be effected using methods which are well known in the art. Examples of such methods include, but are not limited to, Western blot, Radio-immunoassay (RIA), Fluorescence activated cell sorting (FACS), and Immunohistochemical analysis.

Alternatively, detection of sFlt-14 may be at the polynucleotide level. To this end, the sample is contacted with an isolated polynucleotide (e.g., oligonucleotide) which comprises a nucleic acid sequence which specifically binds to sFlt-14 (SEQ ID NO: 1 or 3 or to a bridging sequence as, for example, as set forth in SEQ ID NO: 8) and not to sFlt-1 (SEQ ID NO: 9) so as to form a hybridization complex.

Following a sufficient time of incubation the presence or level of the complex is measured to thereby detect sFlt-14 in the biological sample.

For example, oligonucleotides can be used which are capable of binding to sequences which are specific to sFlt-14 polynucleotides and not to other Flt-1 polynucleotides (e.g. membrane-anchored Flt-1 and soluble Flt-1) such as sFlt-1 (SEQ ID NO: 9). Such sequences may be present in the untranslated region or the open reading frame of the isolated polynucleotides.

As used herein, the term "oligonucleotide" refers to a single-stranded or double-stranded oligomer or polymer of ribonucleic acid (RNA) or deoxyribonucleic acid (DNA) or mimetics thereof. This term includes oligonucleotides composed of naturally occurring bases, sugars, and covalent internucleoside linkages (e.g., backbone), as well as oligonucleotides having non-naturally occurring portions, which function similarly to respective naturally occurring portions.

As used herein, the phrase "capable of specifically hybridizing" refers to forming a double strand molecule such as RNA:RNA, RNA:DNA and/or DNA:DNA molecules.

Oligonucleotides designed according to the teachings of the present invention can be generated according to any oligonucleotide synthesis method known in the art, such as enzymatic synthesis or solid-phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

The oligonucleotide of the present invention is of at least 17, at least 18, at least 19, at least 20, at least 22, at least 25, at least 30 or at least 40, bases specifically hybridizable with polynucleotide sequences of the present invention.

Hybridization based assays which allow the detection of a DNA or RNA of interest in a biological sample rely on the use of oligonucleotide which can be 10, 15, 20, or 30 to 100 nucleotides long preferably from 10 to 50, more preferably from 40 to 50 nucleotides.

Hybridization of short nucleic acids (below 200 bp in length, e.g. 17-40 bp in length) can be effected using the following exemplary hybridization protocols which can be modified according to the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$; (ii) hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$, final wash solution of 6×SSC, and final wash at 22° C.; (iii) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature.

The detection of hybrid duplexes can be carried out by a number of methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample (target).

For example, oligonucleotides of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, Fluor X (Amersham) and others [e.g., Kricka et al. (1992), Academic Press San Diego, Calif] can be attached to the oligonucleotides.

Traditional hybridization assays include PCR, RT-PCR, RNase protection, in-situ hybridization, primer extension, Northern Blot and dot blot analysis (see Examples section hereinbelow).

It will be appreciated that detection of sFlt-14 may also be effected by other methods which do not include the use of antibodies or oligonucleotides. These methods, even if more laborious at time, include but are not limited to molecular weight-based identification and mass spectrometry.

It will be appreciated that the above described methods of detecting sFlt-14 is mostly desired for the diagnosis of a pregnancy associated medical condition associated with maternal or fetal stress.

As used herein the term "diagnosis" refers to classifying a disease or a symptom, determining a severity of such a disease, monitoring disease progression, monitoring the effectiveness of a therapeutic regime, forecasting (prognosing) an outcome of a disease and/or prospects of recovery.

As used herein the phrase "a pregnancy associated medical condition associated with maternal or fetal stress" refers to a disease or a syndrome in which there are clinical symptoms in the mother of fetus which are associated with upregulation of sFlt-14. The pregnancy may be at any stage or phase. The medical condition may include any hypertensive disorders: preeclampsia, eclampsia, mild preeclampsia, chronic hypertension, EPH gestosis, gestational hypertension, superimposed preeclampsia (including preeclampsia superimposed on chronic hypertension, chronic nephropathy or lupus), HELLP syndrome (hemolysis, elevated liver enzymes, low platelet count) or nephropathy. The medical condition may also include gestational diabetes, fetal growth restriction (FGR) and fetal alcohol syndrome (FAS).

As used herein, the phrase "maternal or fetal stress" refers to any condition in which the mother or the fetus is at risk of developing a pregnancy related complication. Fetal stress includes, without being limited to, inadequate nutrient supply and cessation of fetal growth. Maternal stress includes, without being limited to, hypertension and diabetes. Fetal and maternal stress may affect fetal development and brain functions and plays a significant role in pregnancy outcomes related to prematurity and urgent deliveries (e.g. c-section).

As used herein the phrase "subject in need thereof" refers to a mammal preferably a human subject (e.g., pregnant female or a fetus).

Although this invention is described with respect to pregnant women, methods described herein may also be utilized to assess the risk to non-pregnant women of developing hypertensive disorders during pregnancy.

As mentioned herein above, the present inventors have shown that sFlt-14 is significantly upregulated in preeclampsia (see Example 3 and FIGS. 4A-B). Furthermore, the present inventors have shown that the novel VEGFR variant (sFlt-14) is expressed from early pregnancy (weeks 9) and is the dominant VEGFR starting from the second trimester (week 13, see Example 8 and FIGS. 9A-B). Thus, the present inventors envision the use of agents capable of downregulating sFlt-14 for the treatment of pregnancy associated medical conditions. In addition the present inventors have successfully shown that the novel variant competes with VEGFR (see Example 9 and FIG. 10B) to binding of VEGF and as such regulation of the novel variant is critical for the treatment of VEGF-associated medical conditions.

As used herein "a VEGF associated medical condition" refers to a disease, disorder or condition which onset or progression of depend on reduced or excessive activity or expression of VEGFR ligands as described above.

Thus, according to some embodiments of the present invention there is provided a method of treating a VEGF-associated medical condition in which there is a reduced activity and/or expression of VEGF. The method comprising administering to a subject in need thereof a therapeutically effective amount of an agent capable of downregulating sFlt-14 to thereby treat the VEGF-associated medical condition in the subject.

Examples of medical conditions associated with reduced activity and/or expression of VEGF include, but are not limited to, preeclampsia, gestational diabetes, gestational hypertension, fetal growth restriction (FGR), fetal alcohol syndrome (FAS) and hypertension.

As used herein "treating" refers to preventing, curing, reversing, attenuating, alleviating, minimizing, suppressing or halting the deleterious effects of a medical condition.

Examples of such agents include the above-described antibodies and polynucleotides (e.g., capable of specifically binding and inhibiting sFlt-14 and not sFlt-1).

For example, the agent of this aspect of the present invention may be capable of reducing activity and/or expression (i.e. downregulating) sFlt-14 by affecting the cells which produce the sFlt-14 polypeptides (e.g. trophoblasts).

Thus, an agent capable of downregulating sFlt-14 of the present invention is an oligonucleotide capable of specifically hybridizing (e.g., in cells under physiological conditions) to a polynucleotide comprising a nucleic acid sequence encoding a sFlt-14 polypeptide. Such oligonucleotides have been described hereinabove.

Delivery strategies which can be used to efficiently deliver oligonucleotides into a wide variety of cell types are well known in the art [see, for example, Luft J Mol Med 76: 75-6 (1998); Kronenwett et al., Blood 91: 852-62 (1998); Rajur et al., Bioconjug Chem 8: 935-40 (1997); Lavigne et al., Biochem Biophys Res Commun 237: 566-71 (1997) and Aoki et al., (1997) Biochem Biophys Res Commun 231: 540-5 (1997].

An example of an oligonucleotide agent capable of downregulating the expression of sFlt-14 polypeptides is a small interfering RNA (siRNA) molecule. RNA interference is a two-step process. During the first step, which is termed the initiation step, input dsRNA is digested into 21-23 nucleotide (nt) small interfering RNAs (siRNA), probably by the action of Dicer, a member of the RNase III family of dsRNA-specific ribonucleases, which cleaves dsRNA (introduced directly or via an expressing vector, cassette or virus) in an ATP-dependent manner. Successive cleavage events degrade the RNA to 19-21 bp duplexes (siRNA), each strand with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al., (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs, which would generate more siRNAs, or by replication of the siRNAs formed. Alternatively or additionally, amplification could be effected by multiple turnover events of the RISC [Hammond et al., Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the sFlt-14 polynucleotide sequence target is scanned downstream for AA dinucleotide sequences. Occurrence of each AA and the 3' adjacent 19 nucleotides is recorded as potential siRNA target sites.

Second, potential target sites are compared to an appropriate genomic database (e.g., human, mouse, rat etc.) using any sequence alignment software, such as the BLAST software available from the NCBI server (wwwdotncbidotnlmdotnihdotgov/BLAST/). Putative target sites that exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Other nucleic acid agents which can be used to down-regulate expression of sFlt-14 include but are not limited to a DNAzyme molecule capable of specifically cleaving its encoding polynucleotide. DNAzymes are single-stranded polynucleotides which are capable of cleaving both single and double stranded target sequences (Breaker, R. R. and Joyce, G. Chemistry and Biology 1995; 2: 655; Santoro, S. W. & Joyce, G. F. Proc. Natl, Acad. Sci. USA 1997; 94:4262); a ribozyme molecule capable of specifically cleaving its encoding polynucleotide. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications; a triplex forming oligonucleotides (TFOs). In the last decade, studies have shown that TFOs can be designed which can recognize and bind to polypurine/polypirimidine regions in double-stranded helical DNA in a sequence-specific manner. Thus the DNA sequence encoding the polypeptide of the present invention can be targeted thereby down-regulating the polypeptide.

Downregulating sFlt-14 can also be effected at the protein level.

Thus, another example of an agent capable of downregulating a polypeptide of the present invention is an antibody or antibody fragment capable of specifically binding sFlt-14 or a homologue thereof, preferably to its active site, thereby preventing its function. Methods of producing such antibodies are described hereinabove.

Regardless of the agents employed, the effect of same on sFlt-14 activity and/or expression (and indirectly VEGF activity or expression) may be determined using well known molecular biology, biochemical or cell biology techniques. The specific assay will be selected according to the particular researcher's needs and expertise.

As mentioned hereinabove, soluble VEGF receptors bind and antagonize VEGF activity. Indeed, the present inventors have further shown that sFlt-14 antagonizes VEGF (Example 9 and FIG. 10B).

Thus, according to some embodiments of the present invention there is provided a method of treating a VEGF-associated medical condition in which there is an excessive activity and/or expression of VEGF (such an excessive activity or expression often results in hyperangiogenesis). The method comprising administering to a subject in need thereof a therapeutically effective amount of an agent capable of upregulating sFlt-14 to thereby treat the VEGF-associated medical condition in the subject.

Examples of medical conditions associated with excessive activity and/or expression of VEGF include, but are not limited to, cancer, eye disorders such as neovascularization of the cornea, polycystic ovary disease and endometriosis.

As such, the present invention envisions use of the novel sFlt-14 for antagonizing VEGF activity and thereby reducing angiogenesis which may be harnessed for the treatment of VEGF associated conditions (e.g., cancer).

As used herein the term "angiogenesis" refers to the production or development of blood vessels.

As used herein the term "cancer" refers to any tumoral disease including metastasis. Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lymphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Endometrial cancer, Malignant melanoma, Mesothelioma, breast, skin, prostate, and ovarian.

As used herein the phrase "neovascularized cornea" refers to the abnormal, pathological condition in which the cornea becomes vascular.

Other medical conditions, diseases and disease processes in which angiogenesis plays a role can be treated according to the teachings of the present invention. These include, but are not limited to, diabetic retinopathy, neovascular glaucoma, rheumatoid arthritis and hemangiomas.

Agents capable of upregulating the polypeptides of the present invention, which may be used for the treatment of VEGF associated conditions (e.g., cancer or corneal neovascularization), comprise the isolated polypeptides per se or polynucleotides of the present invention.

Thus, polynucleotides of the present invention can be administered to the subject employing any suitable mode of administration, described hereinbelow (i.e., in vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

Such polynucleotide sequences are typically inserted into expression vectors to enable expression of the recombinant polypeptide. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

To enable cellular expression of the polynucleotides of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

The nucleic acid construct of the present invention may further include an appropriate selectable marker and/or an origin of replication. For example, the nucleic acid construct utilized may be a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMT010/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Recombinant viral vectors may also be used to synthesize the polynucleotides of the present invention. Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Bone marrow cells can be targeted using the human T cell leukemia virus type I (HTLV-I).

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

It will be appreciated that up-regulating the expression and/or function of a sFlt-14 polypeptide will typically result in a reduced VEGF activity.

The above described agents of the present invention can be provided to the individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the isolated polypeptides, the isolated polynucleotides, or the antibody preparations, which are accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It is expected that during the life of a patent maturing from this application many relevant polypeptides and polynucleotides encoding sFlt-14 will be developed and the scope of the term polypeptides and polynucleotides encoding sFlt-14 is intended to include all such new technologies a priori.

As used herein the term "about" refers to ±10%

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Sequence of the Novel sFlt-14

Materials and Experimental Procedures
RNA
Placental tissue was homogenized with a Polytron homogenizer and preceded the total RNA extraction in TRI Reagent (Sigma) according to the manufacturer's protocol. Cells were harvested and RNA was extracted in TRI Reagent.
RACE
Rapid Amplification of cDNA Ends was preformed using BD SMART™ RACE cDNA amplification kit. 3' RACE based on preeclamptic placental RNA was used with a primer taken from the beginning of FLT1's exon 14 used as the 5' primer CCTCCTGCGAAACCTCAGTG (SEQ ID NO: 12) and a 3' primer that was supplied with the RACE kit: AAGCAGTGGTATCAACGCAGAGTAC(T)$_{30}$VN (SEQ ID NO: 11).
Results
As is illustrated in FIGS. 1-3, the novel sFlt1 of the present invention differs from the full transmembrane receptor Flt1 and from the known sFlt1 in the following three aspects:
1) sFlt-14 does not comprise the 31 amino acids unique to sFlt-1 (derived from intron 13) as clear from FIG. 1 (marked by the light coloring).
2) sFlt-14 contains RNA sequences, as well as an amino acid stretch, not present in sFlt-1. The amino acid sequence includes amino acids derived from exon 14 (which are also present in the full transmembrane receptor, see FIG. 1) as well as a unique amino acid sequence derived from intron 14 (marked by the light coloring, see FIG. 1). As shown in FIG. 3A, this unique sequence comprises a stretch of 28 amino acids derive from intron 14.
3) As shown in FIG. 2A, sFlt-14 also contains a unique regulatory sequence, namely a 3'-UTR fully derived from intron 14, including an Alu element contained within its 3'-UTR.
Furthermore, as is illustrated in FIG. 2A, the cDNA sequence that is unique to the novel sFlt-14 comprises sequences not present in cDNAs from either the full transmembrane Flt1 or from the soluble sFlt-1. A search throw database revealed several EST sequences deposited in data bases where only fragments of this unique transcript were identified (FIG. 2B). However, this alternatively-spliced sequence variance of Flt (namely sFlt-14 of the present invention) was not mentioned previously in the published literature, let alone association with any tissue or pathology.

Example 2

Generation of sFlt-14 Specific Antibodies

Materials and Experimental Procedures
Generation of sFlt-14 Specific Polyclonal Antibodies
Polyclonal antibodies were generated as described in the Sigma-Aldrich's protocol. In short, two peptides derived from sFlt-14 were synthesized (CHFK, SEQ ID NO: 6 and CESS, SEQ ID NO: 5) and injected into rabbits in order to produce anti sFlt-14 sera. Three injections for each peptide were performed, with a month period kept between injections. At the end of this procedure rabbit serums were evaluated for sFlt-14 reactivity.

Results

Two short peptides were generated from the amino acid sequence which distinguishes the novel sFlt-14 of the present invention from the previously described sFlt-1. As illustrated in FIG. 3B, the first peptide, termed CHFK (SEQ ID NO: 6), which was derived from exon 14, is not comprised in sFlt-1 but is present in the full transmembrane receptor. The second peptide, termed CESS (SEQ ID NO: 5), was derived from a sequence unique only to the novel sFlt-14 (and is not comprised in either the transmembrane Flt-1 or sFlt-1). These two peptides were used to elicit polyclonal antibodies as described in the experimental description hereinabove.

The polyclonal antibodies generated can distinguish between the novel sFlt-14 and the previously described sFlt-1.

Example 3

Relative Abundance of Transmembrane Flt-1, sFlt-1 and sFlt-14 in Different Cells Materials and Experimental Procedures
Cells Cells were obtained and cultured as previously described in Gluzman et al. [Gluzman et al., Biochem Biophys Res Commun. (2007) 359:263-8].

RNA

Normal placenta tissue and preeclampsia placenta tissue were homogenized with a Polytron homogenizer and preceded the total RNA extraction in TRI Reagent (Sigma) according to the manufacturer's protocol. Cells were harvested and RNA was extracted in TRI Reagent.

Northern Blotting

Total RNA (5-20 µg) was resolved by formaldehyde-agarose (1%) denaturing gels and blotted to positively charged nylon membrane by capillary elution. The RNA was UV crosslinked (1200 j/m2) and the membrane was stained with 0.1% methylene blue to ensure equal loading and transfer. Blots were hybridized overnight with a $^{32}$P-labeled probe by a rediprime kit (Amersham). The blots were subjected to two washes (with 2×SSC, 1% SDS) for 30 minute at 60° C., after which they were exposed to MS sensitive film (Kodak). Three different probes from different regions of the FLT1 transcripts were used in order to allow detection of the various FLT1 isoforms: 1) an extra-cellular coding region for the detection of all the isoforms; 2) an intron 14 region for the detection of sFLT-14; and 3) an intron 13 region for the detection of sFLT1.

Results

As illustrated in FIG. 4A, RNA obtained from HUVEC, normal placenta and preeclampsia placenta were separated on an RNA blot and hybridized with a probe common to Flt-1, sFlt-1, and sFlt-14 (which were distinguished by the band position). As evident from the results, in endothelial cells, known as the 'traditional' cells expressing VEGF receptors, the predominant soluble Flt is sFlt-1 (also termed herein sFlt-13). In sharp contrast, in placenta the predominant soluble receptor is the novel sFlt-14 of the present invention. The identity of the respective splice variant was further validated through re-probing with probes specific for sFlt1 and for sFlt-14 (data not shown).

Likewise, a comparison between endothelial cells and vascular smooth muscle cells shows that whereas endothelial cells predominantly express sFlt-1, vascular smooth muscle cells predominantly express the novel sFlt-14 (FIG. 4B). sFlt-14 has also been demonstrated as the predominant, if not the exclusive, Flt isoform present in trophoblasts and dendritic cells (data not shown). Taken together these results indicate that sFlt-14 may be viewed as non-endothelial cell-specific, whereas, sFlt1 as the variant present in endothelial cells.

It is important to note that since alternative splicing which generates the full receptor or, alternatively, the soluble receptor (either variant) are mutually exclusive, the following occurs: In case sFlt1 is generated (e.g. by endothelial cells), the ratio of membrane-spanning Flt1 receptor to soluble Flt1 receptor is high. In contrast, the alternative splicing mode which generates sFlt-14, allows the dominancy of sFlt14 over the membrane spanning Flt1 receptor. This results in a net transition from pro- to anti-VEGF signaling and renders the expressing cells irresponsive to VEGF.

Example 4

In Situ Protein and mRNA Detection of sFlt-14 in Preeclamtic Placenta

Materials and Experimental Procedures
In Situ Hybridization

Placental paraffin embedded sections were hybridized with a S35 riboprobe taken from the intron 14 region of sFlt-14 (SEQ ID NO: 13) as was previously described by Motro et al. [Motro et al., PNAS, 1990, 87(8), 3092-6].

Immunohistochemistry

A sFlt-14 specific rabbit polyclonal antibody at a 1:100 dilution was used on paraffin embedded placental sections. Antigen retrieval was carried out using 25 mM citrate buffer pH=6.0. The antibody was directed against a peptide derived from the C-terminus of the sFLT-14 protein—CELYTST-SPSSSSSS (CESS antibody, SEQ ID NO: 5).

Results

FIGS. 5A-B demonstrate the major value of the CESS antibody directed specifically against the unique section of sFlt-14 (the amino acids of intron 14) as illustrated in immunohistological detection of sFlt-14 proteins in placental sections. Likewise, FIGS. 5C-D demonstrate the importance of the unique mRNA probe (complementary to the unique intron 14 sequence) for specific detection of sFlt-14 mRNA as illustrated by in situ hybridization of placental sections with the specific probe. It should be emphasized that there is no cross-reaction of the CESS antibody or of the probe with the full receptor Flt and the soluble sFlt-1 so that the reagents are truly exclusive for the novel sFlt-14.

FIGS. 5A-D also provide some mechanistic insights to the pathogenic process as these results identify, for the first time, which cells in the diseased placenta produce the soluble receptor (cells that were not identified using the known sFlt1). These findings illustrate that trophoblastic cells within the syncytial knots produce the soluble sFlt-14. These results are consistent with the fact that syncytial knots are much more abundant in pre-eclampsia compared to normal pregnancy, and are a hallmark of a degenerative placenta.

Example 5

Expression of sFlt-14 in Normal Term Placentae

Materials and Experimental Procedures
Western Blotting

Three normal term placentae were homogenized and separated into two groups: group 1) subjected to a pre immune cleaning treatment; and group 2) not subjected to cleaning treatment. The cleaning treatment (used to clean the sample from proteins that might interact with the irrelevant antibodies of the CESS serum in the detection step) included 3 hour incubation with 20 μl rabbit pre-immune serum followed by an addition of Protein A beads (P3391, Sigma), overnight incubation and precipitation. The non-cleaned treatment was the same, without the addition of rabbit pre-immune serum.

Each sample, cleaned or non-cleaned, was separated into two different immunoprecipitations, one with the CESS antibody and the other with the FLT11 antibody (V4262, Sigma). The precipitants were loaded on a 6% acrylamide gel, run electrophoretically, transferred to a membrane and detected with the CESS antibody.

Results

As clearly illustrated in FIG. 6, the size of the sFLT14 protein is approximately 110 Kd. It is precipitated by the FLT11 antibody, which targets the extracellular domain of Flt-1, and visualized by the CESS antibody, which specifically targets the C' terminus of the novel sFlt-14, validating the existence of a novel variant of the soluble Flt1. These results also proved that the unique CESS epitope is an integral part of a splice variant that includes the extracellular binding domain of Flt1.

Example 6

Mass-Spectrometry Identification of sFLT14

Materials and Experimental Procedures
Mass Spectrometry

A preeclamptic placenta was homogenized in a protein lysis buffer, and incubated for 3 hours with 20 μl rabbit pre-immune serum (in order to clean the sample from proteins that might interact with the irrelevant antibodies of the CESS serum). Protein A beads (P3391, Sigma) were added for overnight incubation and precipitated. 15 μl CESS antibody was added to the cleaned homogenate, incubated for 3 hours, followed by an addition of protein A beads and another overnight incubation. The beads were precipitated, washed, and boiled with sample buffer. The samples were loaded on a 6% acrylamide gel and run electrophoretically. The gel was stained with coomassie blue and destained till bands appeared. A 110 Kd band was cut for mass spectrometry analysis. The band was digested by trypsin, analyzed by LC-MS/MS on DECA/LCQ and identified by Pep-Miner and Sequest software against nr database of human, mouse, rat, bovine and rabbit.

Results

As depicted in FIG. 7, a positive identification of Flt1 was achieved by three peptides taken from the extracellular domain of Flt1. These results proved that the extracellular domain of Flt1 and the C' terminus of the novel sFlt-14 are on the same continuity. Eight amino-acids of the DQEAPYLLR peptide (QEAPYLLR, SEQ ID NO: 19) are encoded by exon 14, further strengthening the inclusion of exon 14 in the novel C' terminus.

Example 7

Presence of sFlt-14 Isoforms in Serum of Preeclamptic Subjects

Materials and Experimental Procedures
Analysis of Serum Proteins 20 ml serum samples from PE subjects were concentrated via capture on FLT11-coated beads and elution. Affinity-purified proteins were analyzed by Western-blotting. Accordingly, proteins were separated on 6% acrylamide gel, electrophoretically transferred to a membrane, and immunoblotted with the sFlt-14 specific CESS antibody. Protein detection was carried out using CESS antibody or the ab9540 antibody.

Results

Following the novel results illustrating that PE placentae express upregulated levels of sFlt-14 (Examples 3 and 4 hereinabove), inventors of the present invention investigated which sFlt isoform accumulates in the serum of PE subjects. To identify the characteristics of circulating soluble receptors, inventors of the present invention analyzed preeclamptic serum specimens. This was done by affinity purifying sFlt isoforms from serum of PE patients with the FLT11 extracellular antibody. The purified isoforms were western blotted next to a CESS immunoprecipitate of the placenta using the specific sFlt-14 antibody (CESS antibody). As illustrated in FIG. 8, the same two protein bands were detected in the placenta and serum of PE subjects. These two proteins were previously identified as sFlt-14 proteins (Example 3, hereinabove). Furthermore, the sFlt-14 protein detected in the serum of PE subjects was visualized as two bands identical in size to those produced by cells transfected with sFlt-14 expression plasmid (see Example 10 hereinbelow) and detected with the sFlt-14-specific antibody. A second immunoblotting using the ab9540 extracellular targeting antibody failed to give different bands than the two mentioned above (data not shown), thus eliminating sFlt-1 existence in the PE serums that were tested, indicating that sFlt-14 is the major VEGF receptor in the circulation of PE subjects.

Example 8 sFLT-14 is the Exclusive sFLT1 Isoform from the Second Trimester of Pregnancy

Materials and Experimental Procedures
Northern Blotting

Total RNA was generated from human placental biopsies at different time points of gestation (weeks 9-11, 13 and 39 of gestation). 10-15 μg RNA of each sample was resolved by formaldehyde-agarose (1%) denaturing gels and blotted to positively charged nylon membrane by capillary elution. The RNA was UV crosslinked (1200 j/m2) and the membrane was stained with 0.1% methylene blue to ensure equal loading and transfer. Blots were hybridized overnight with a $^{32}$P-labeled probe by a rediprime kit (Amersham). The probe used (SEQ ID NO: 14) targeted the shared sequences of both isoforms, thus able to show their relative abundance. The blots were subjected to two washes (with 2×SSC, 1% SDS) for 30 minute at 60° C., after which they were exposed to MS sensitive film (Kodak).

Results

In order to characterize the relative contribution of each of the sFLT1 isoforms during the normal course of gestation, RNA was generated from human placental biopsies at different time points during the course of normal gestation and an extracellular probe targeting the shared sequences of both isoforms was used for hybridization (see materials and experimental section above). As illustrated in FIGS. 9A-B, weeks 9-11 of gestation (first trimester) are characterized by a 1:1 ratio of the sFlt-1 and sFlt-14 isoforms. However, at week 13 of gestation (beginning of the second trimester) sFlt-14 becomes the dominant, if not the exclusive isoform expressed in placentae. Furthermore, at week 39 (third trimester) sFlt-14 remains the exclusive isoform. The exclusive expression of sFLT-14 from the second trimester of pregnancy and onward corresponds to the fact that sFLT-14 is significantly upregulated in preeclampsia (a condition that usually occurs during the third trimester of pregnancy).

Example 9 sFLT-14 is a Potent VEGF Inhibitor

Materials and Experimental Procedures
Expression of Recombinant sFlt1 and sflt-14 Proteins in Hela Cells cDNAs encompassing the entire coding region of both soluble receptor isoforms sFlt-14 and sFlt-1 (SEQ ID NOs: 1 and 9, respectively) were sub-cloned into Bluescript expression vectors and transfected into T7 polymerase-expressing human Hela cells. 20-24 hours later, growth media were collected and cells were harvested. Secreted proteins and cell associated proteins were immunoprecipitated with the FLT11 antibody (V4262, Sigma) and analyzed by immunoblotting with antibodies (Ab9540, Abcam) directed against the extracellular domain of both sFlt-1 and sFlt-14.

ELISA

Analysis of sFlt-1 and sFlt-14 secretion of into the growth medium was carried out using ELISA directed against a shared extracellular epitope using DVR100 (R&D systems).

Immunoprecipitation and Western Blotting sFlt-1 and sFlt-14 secretion into the growth medium was analyzed by immunoprecipitation with the FLT11 antibody and western immunoblotting was carried out with the ab9540 antibody. Western blotting was further carried out as described in Example 5.

VEGF Inhibition Assay

Porcine Aortic Endothelial (PAE) cells engineered to express high levels of human VEGF-R2 were acquired from Prof. Gera Neufeld (Technion, Haifa, Israel). Cells were grown in 10% FCS DMEM growth medium.

Increasing amounts of sFlt-14 or sFlt-1 (20, 40, 80 ng/ml) were pre-incubated with a constant amount of VEGF (20 ng/ml) prior to adding the growth medium of PAE cells. VEGF-R2 phosphorylation levels were measured as a function of added sFlt-14/VEGF ratio or sFlt-1/VEGF ratio. A reduction in VEGF-R2 phosphorylation was determined using antibodies detecting phospho-VEGF-R2 (Cell-signaling, Cat. #2478) and standardized to total VEGF-R2 protein visualized by immunoblotting with anti-VEGF-R2 antibody (Santa Cruz Cat. SC-504).

Results

Since sFlt1 and sFlt-14 are qualitatively different proteins (sFlt-14 contains 75 amino acids not present in sFlt1 and sFlt1 contains 31 highly-conserved amino acids not present in sFlt-14), inventors of the present invention wished to demonstrate that sFlt-14 is in fact a VEGF receptor capable of specifically binding and antagonizing VEGF.

To this end, inventors generated sFlt-14 expressing human Hela cells and, for comparison, generated sFlt1-expressing Hela cells. ELISA analysis (directed against a shared extracellular epitope) has indicated that the secretion of sFlt-1 and sFlt-14 into the respective growth medium was comparable (concentrations of 100-200 ng/ml were detected for both, data not presented). Furthermore, inventors confirmed the mutually exclusive presence of either sFlt-14 or sFlt-1 in the respective growth media by immunoprecipitation and western blots, as evident by the apparent molecular size of the immunoreactive protein (130 Kd and 120 Kd, respectively, FIG. 10A).

To determine whether sFlt-14 inhibits VEGF signaling, increasing amounts of sFlt-14 were pre-incubated with a constant amount of VEGF (20 ng/ml) prior to adding the growth medium of Porcine Aortic Endothelial (PAE) cells engineered to express high levels of human VEGF-R2. VEGF-R2 phosphorylation levels were measured as a function of added sFlt-14/VEGF ratio. As shown in FIG. 10B, nearly complete inhibition of VEGF-R2 phosphorylation was evident already at a 1:1 sFlt-14/VEGF ratio. Conversely, at this ratio, sFlt1 did not significantly inhibit VEGF-R2 phosphorylation and, in fact, inhibited VEGF-R2 phosphorylation only at higher sFlt-1/VEGF ratios. Taken together, these results conclusively showed that sFlt-14 is a potent inhibitor of VEGF signaling and notably more potent than sFlt-1.

Example 10 sFlt-14 is Expressed in Human Cornea

Materials and Experimental Procedures
Immunohistochemistry

Corneal sections were isolated from human corneas that were removed due to a diseased state. A sFlt-14 specific rabbit polyclonal antibody at a 1:100 dilution was used on paraffin embedded corneal sections. Antigen retrieval was carried out using 25 mM citrate buffer pH=6.0. The antibody was directed against a peptide derived from the C-terminus of the sFlt-14 protein—CELYTSTSPSSSSSS (CESS antibody, SEQ ID NO: 5).

Results

It is well known that sFlt-1 plays a major physiological role in the cornea were it a crucial anti-VEGF factor, keeping the cornea avascular, a state which is imperative for clear vision. In mammals, sFlt-1 is expressed by the epithelia of the cornea. In order for the inventors of the present invention to examine whether sFlt-14 is also expressed in the human cornea, specific sFlt-14 antibodies were used for immunohistochemistry of human corneal sections. As clear from FIG. 11A-B, sFlt-14 is highly expressed in the corneal epithelia. The presence of sFlt-14 in the human corneal epithelia was further validated by sFlt-14 PCR analysis of several epithelia samples isolated from human corneas (data not shown).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter for detection of sFlt-14 comprising a biological sample of a pregnant female human subject comprising an antibody capable of binding said sFlt-14 or portion of said sFlt-14 as set forth in SEQ ID NO: 2 or 4 and not sFlt-1 as set forth in SEQ ID NO: 10.

2. The composition-of-matter of claim 1, wherein said biological sample is a blood sample.

3. The composition-of-matter of claim 2, wherein said blood sample is of a gestation week 13 and on.

4. The composition-of-matter of claim 1, wherein said biological sample is selected from the group consisting of a serum sample and a plasma sample.

5. The composition-of-matter of claim 4, wherein said serum sample or said plasma sample is of gestation week 13 and on.

6. The composition-of-matter of claim 1, wherein said antibody is a monoclonal antibody.

* * * * *